(12) United States Patent
Burkhart

(10) Patent No.: US 10,434,086 B2
(45) Date of Patent: Oct. 8, 2019

(54) COMBINATION THERAPIES WITH CURAXINS

(71) Applicant: Incuron, Inc., Buffalo, NY (US)

(72) Inventor: Catherine Burkhart, Buffalo, NY (US)

(73) Assignee: Incuron, Inc., Buffalo, NY (US)

( * ) Notice: Subject to any disclaimer, the term of this patent is extended or adjusted under 35 U.S.C. 154(b) by 207 days.

(21) Appl. No.: 15/302,049

(22) PCT Filed: Apr. 6, 2015

(86) PCT No.: PCT/US2015/024514
§ 371 (c)(1),
(2) Date: Oct. 5, 2016

(87) PCT Pub. No.: WO2015/157172
PCT Pub. Date: Oct. 15, 2015

(65) Prior Publication Data
US 2017/0189379 A1   Jul. 6, 2017

Related U.S. Application Data

(60) Provisional application No. 61/975,865, filed on Apr. 6, 2014.

(51) Int. Cl.
| | |
|---|---|
| *A61K 31/4045* | (2006.01) |
| *A61K 31/7068* | (2006.01) |
| *A61K 45/06* | (2006.01) |
| *A61K 31/404* | (2006.01) |
| *A61K 31/44* | (2006.01) |
| *A61K 31/444* | (2006.01) |
| *A61K 31/506* | (2006.01) |
| *A61K 31/513* | (2006.01) |
| *A61K 31/517* | (2006.01) |
| *A61K 31/706* | (2006.01) |

(52) U.S. Cl.
CPC ........ *A61K 31/4045* (2013.01); *A61K 31/404* (2013.01); *A61K 31/44* (2013.01); *A61K 31/444* (2013.01); *A61K 31/506* (2013.01); *A61K 31/513* (2013.01); *A61K 31/517* (2013.01); *A61K 31/706* (2013.01); *A61K 31/7068* (2013.01); *A61K 45/06* (2013.01)

(58) Field of Classification Search
CPC ............ A61K 31/4045; A61K 31/7068; A61K 31/44; A61K 45/06
See application file for complete search history.

(56) References Cited

U.S. PATENT DOCUMENTS

| | | | |
|---|---|---|---|
| 7,169,802 B2 | 1/2007 | Hudkins et al. | |
| 8,486,697 B2* | 7/2013 | Gudkov | A61K 31/473 |
| | | | 435/173.1 |
| 8,765,738 B2* | 7/2014 | Tucker | C07D 209/86 |
| | | | 514/217.08 |
| 9,108,916 B2* | 8/2015 | Tucker | C07D 209/86 |
| 9,169,207 B2* | 10/2015 | Gudkov | A61K 31/403 |
| 9,566,265 B2* | 2/2017 | Tucker | C07D 209/86 |
| 2005/0143442 A1 | 6/2005 | Hudkins et al. | |
| 2011/0183336 A1 | 7/2011 | Gray et al. | |
| 2011/0305661 A1 | 12/2011 | Tucker et al. | |
| 2014/0066465 A1 | 6/2014 | Stark et al. | |
| 2015/0045406 A1 | 2/2015 | Gudkov et al. | |
| 2016/0303078 A1* | 10/2016 | Bespalov | A61K 31/403 |

FOREIGN PATENT DOCUMENTS

| | | |
|---|---|---|
| DE | 2715680 | 10/1978 |
| WO | 2000002555 | 1/2000 |
| WO | 2004035580 | 4/2004 |
| WO | 2008008155 | 1/2008 |
| WO | 2009143290 | 11/2009 |
| WO | 2010009171 | 1/2010 |
| WO | 2010042445 | 4/2010 |
| WO | 2013148864 | 10/2013 |

OTHER PUBLICATIONS

International Search Report for International Application No. PCT/US2015/024514, dated Jun. 25, 2015, 8 pages.
Di Bussolo, V. et al., "Curaxins: A New Family of Non-Genotoxic Multitargeted Anticancer Agents," ChemMedChem, vol. 6, No. 12, pp. 2133-2136 (Oct. 28, 2011).
Garcia, H. et al., "Expression of FACT in mammalian tissues suggests its role in maintaining of undifferentiated state of cells," Oncotarget, Impact Journals LLC, United States, vol. 2, No. 10, pp. 1-14 (Oct. 1, 2011).
Gasparian, A. V. et al., "Curaxins: Anticancer Compounds that Simultaneously Suppress NF-kappa B and Activate p53 by Targeting FACT," Science Translational Medicine, vol. 3, No. 95, pp. 96-107 (Aug. 2011).
Koman, I. E. et al., "Targeting Fact Complex Suppresses Mammary Tumorigenesis in Her2/neu Transgenic Mice," Cancer Prevention Research, American Association for Cancer Research, United States, vol. 5, No. 8, pp. 1025-1035 (Aug. 1, 2012).
Pieters et al., "Reciprocal Template Effects in Bisubstrate Systems: A Replication Cycle," Tetrahedron, vol. 51, No. 2, pp. 485-498 (May 22, 1994).
Belotserkovskaya et al., "FACT Facilitates Transcription-Dependent Nucleosome Alteration," Science, vol. 301, pp. 1090-1093 (Aug. 22, 2003).
Garcia et al., "Facilitates Chromatin Transcription Complex Is an 'Accelerator' of Tumor Transformation and Potential Marker and Target of Aggressive Cancers," Cell Reports (2013) http://dx.doi.org/10.1016/j.celrep.2013.06.013.

(Continued)

*Primary Examiner* — Lawrence E Crane
(74) *Attorney, Agent, or Firm* — Morgan, Lewis & Bockius LLP

(57) ABSTRACT

Provided herein are methods and compositions that relate to, inter alia, CBL0137, a carbazole compound 1,1'-[9-[2-[(1-methylethyl)amino]ethyl]-9H-carbazole-3,6-diyl]bis-ethanone, useful for the treatment of various cancers, optionally in combination with various agents.

14 Claims, 20 Drawing Sheets
(18 of 20 Drawing Sheet(s) Filed in Color)

(56) References Cited

OTHER PUBLICATIONS

Van Diest et al., "A Scoring System for Immunohistochemical Staining: Consensus report of the Task Force for Basic Research of the EORTC-GCCG", J. Clin. Pathol. 1997, vol. 50, pp. 801-804.
Anonymous: "Curaxin Program Update Investor Day", (Jun. 9, 2010), pp. 1-17. URL:http://content.stockpr.com/cbiolab/media/6c108699838320bef72f)ca555336b7d.pdf.
Gudkov, et al., "Inflammation and p53: A Tale of Two Stresses", Genes & Cancer, vol. 2, No. 4, (Apr. 1, 2011), pp. 503-516.
Hsieh, et al., "Fact in Cell Differentiation and Carcinogenesis", Oncotarget, (Nov. 1, 2011) pp. 830-532.
Bell, et al., "Differential p53 Protein Expression in Breast Cancer Fine Needle Aspirates: The Potential for In Vivo Monitoring", British Journal of Cancer, 2001, vol. 85, No. 8, pp. 1102-1105.
Nakamura, et al., Antitumor Activity of ER-37328, a Novel Carbazole Topoisomerase II Inhibitor. Molecular Cancer Therapeutics, vol. 1, No. 3, (Jan. 1, 2002), pp. 169-175.
Fang et al., "Three-Point Hydrogen Bonding Assembly between a Conjugated PPV and a Functionalized Fullerence", Chem. Mater. 2003, vol. 15, pp. 1593-1597.
Hannig et al., Carbazole Derivatives. III. Aminomethylation of Acylated Carbazoles, Archiv der Pharmazie, vol. 296, No. 8, pp. 536-543, 1963. Abstract only.

* cited by examiner

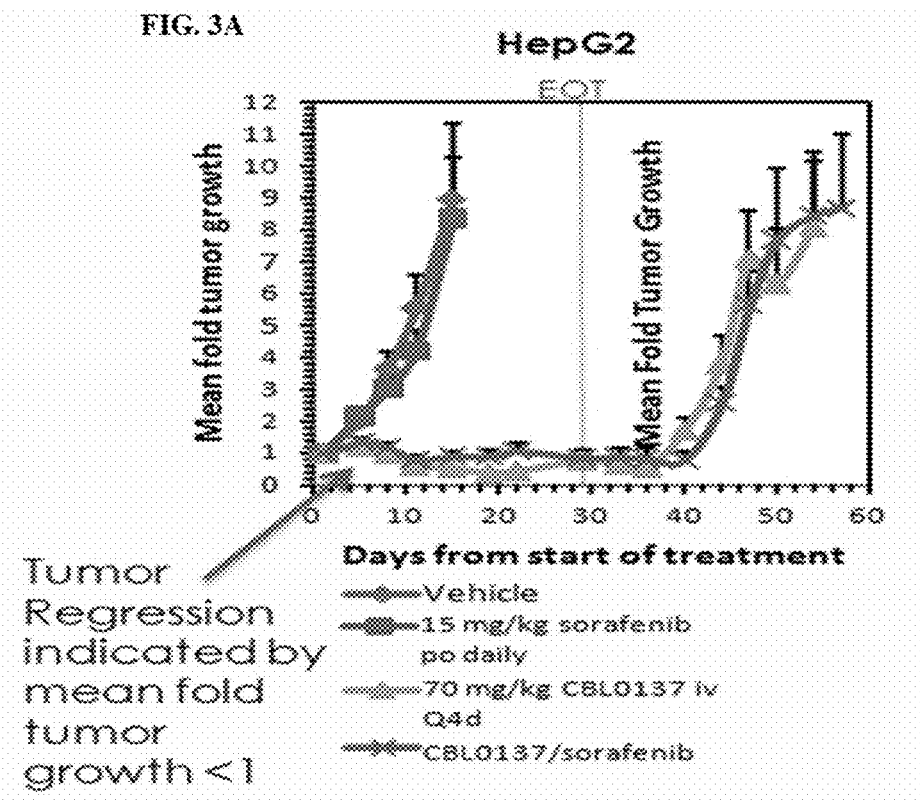

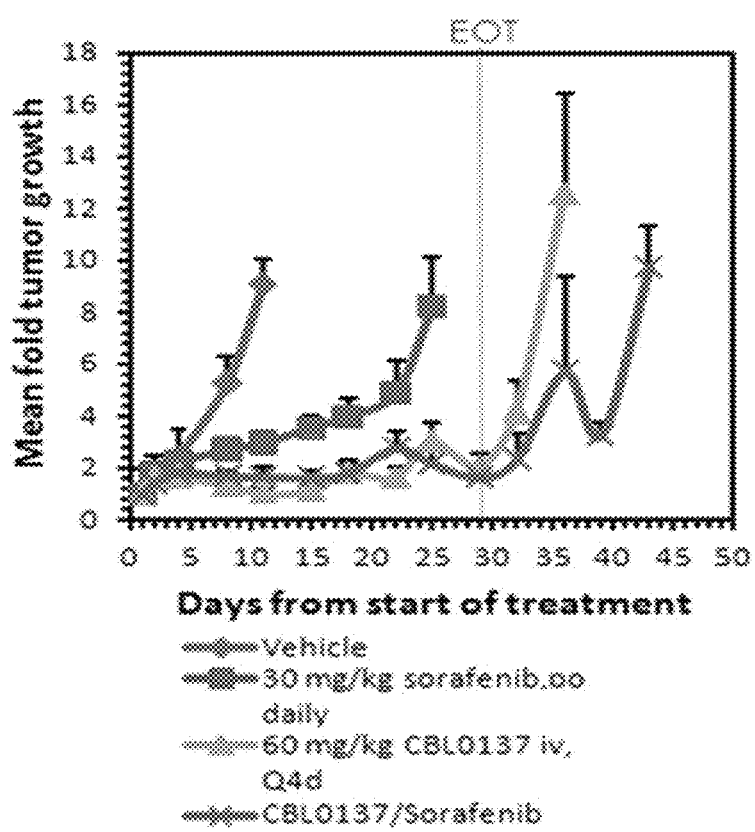

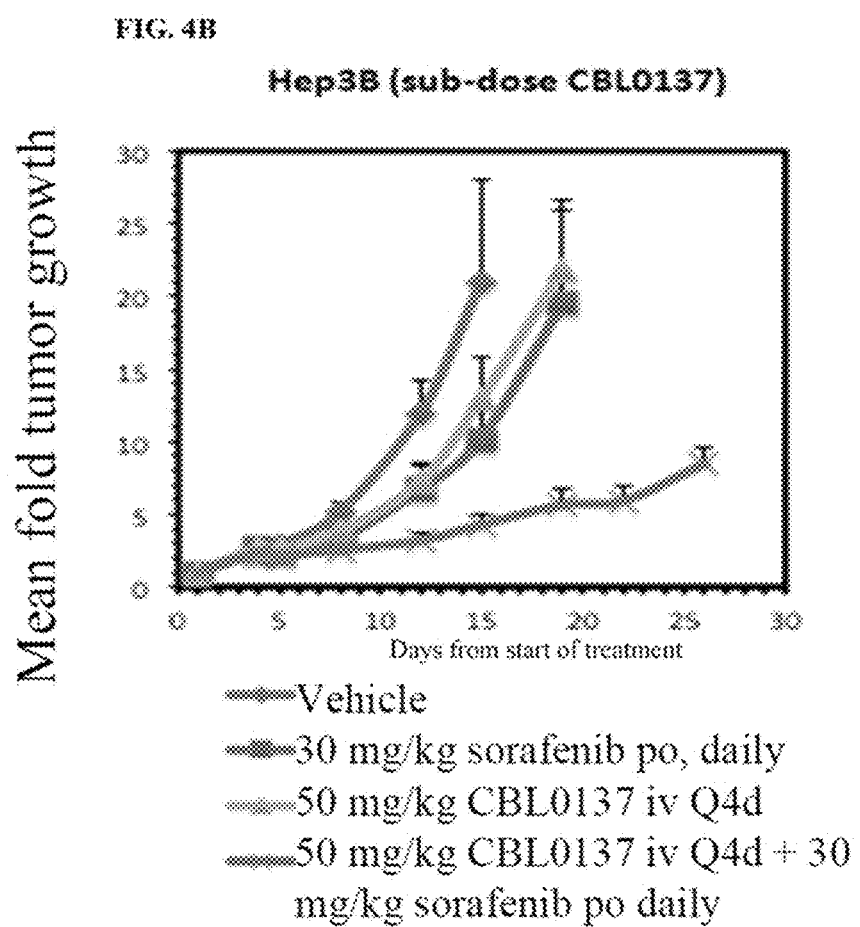

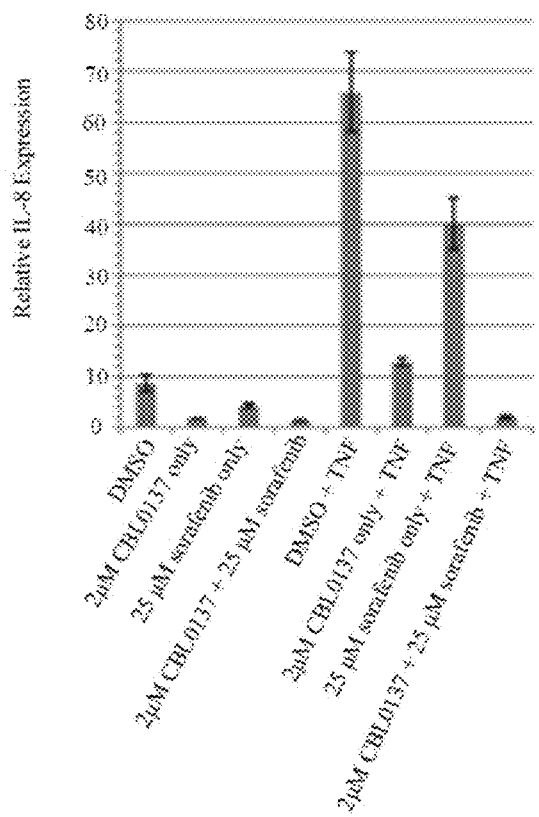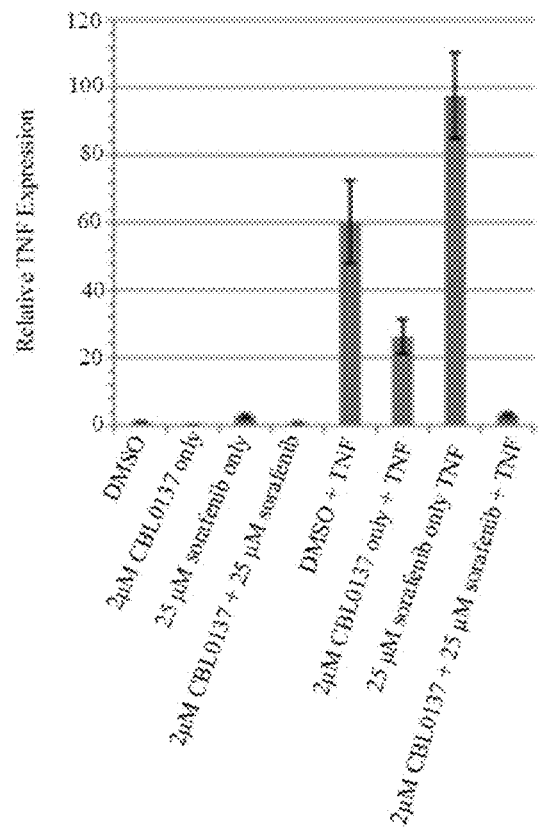
Effect on NF-κB Target Genes
FIG. 6A HepG2 HCC IL-8
FIG. 6B HepG2 HCC TNF

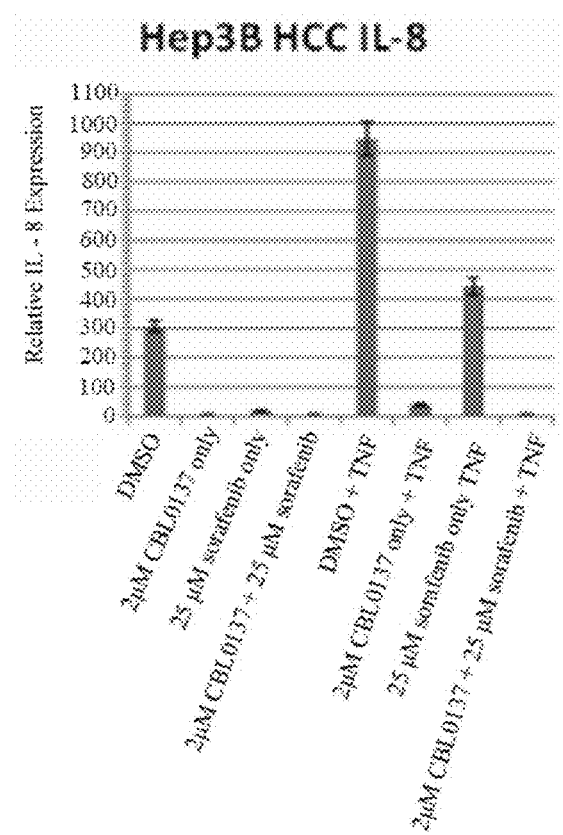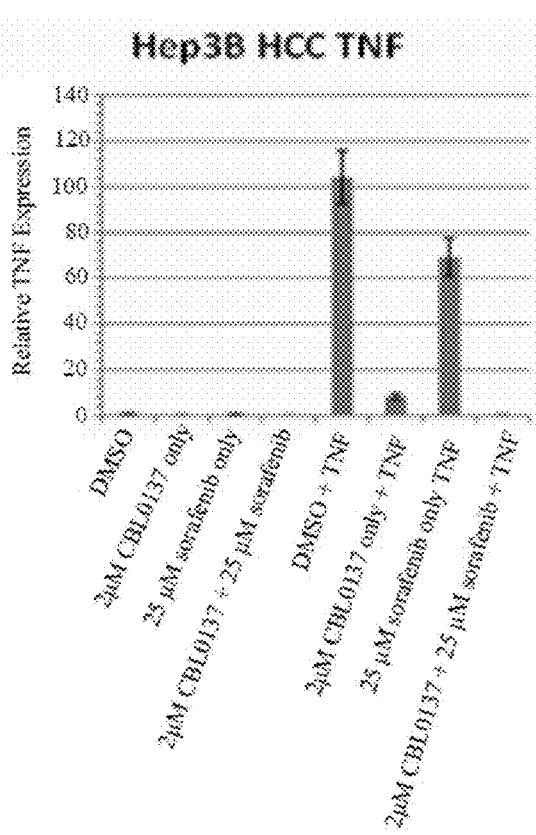

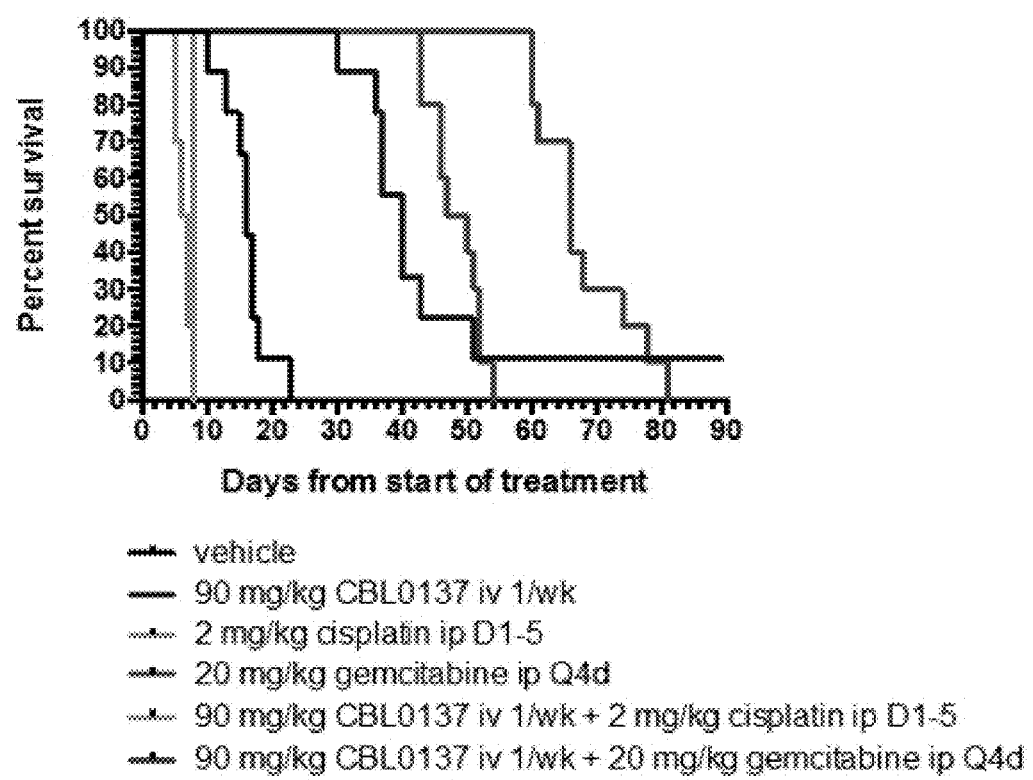

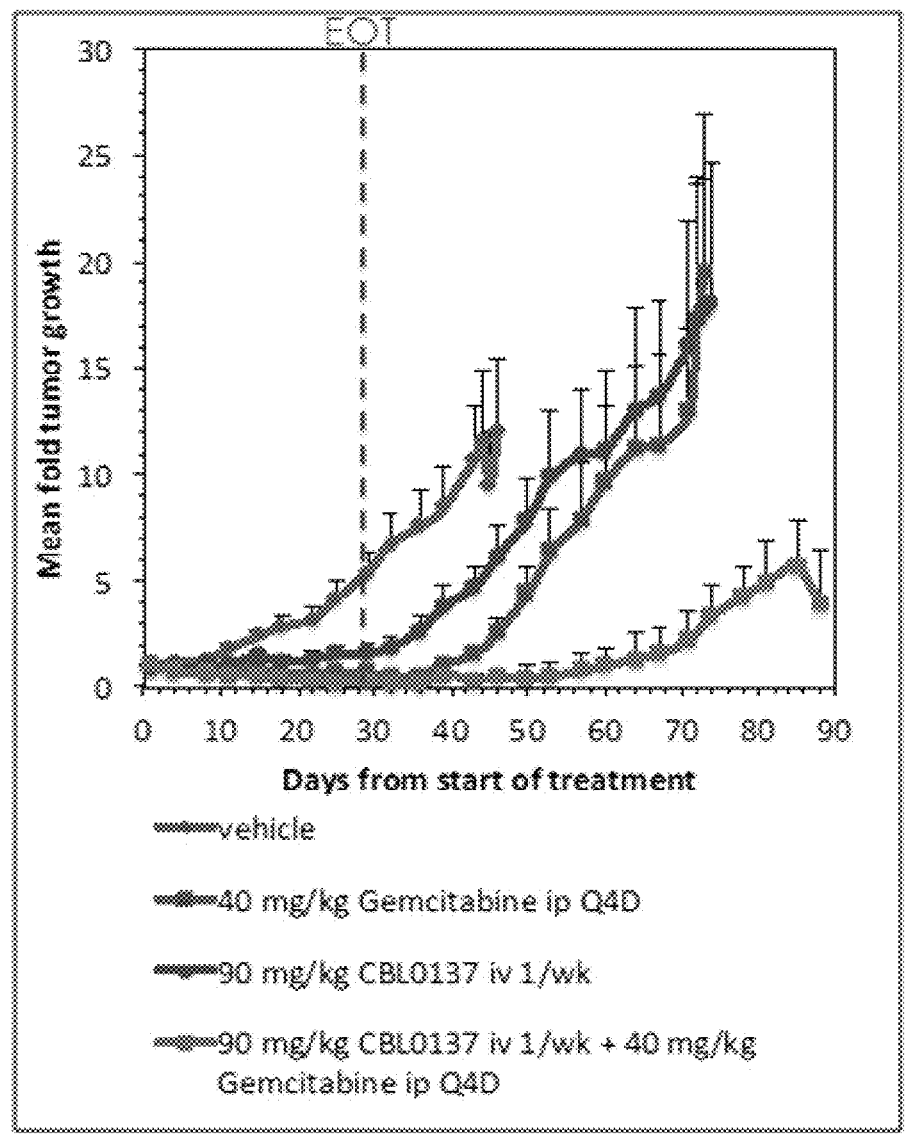

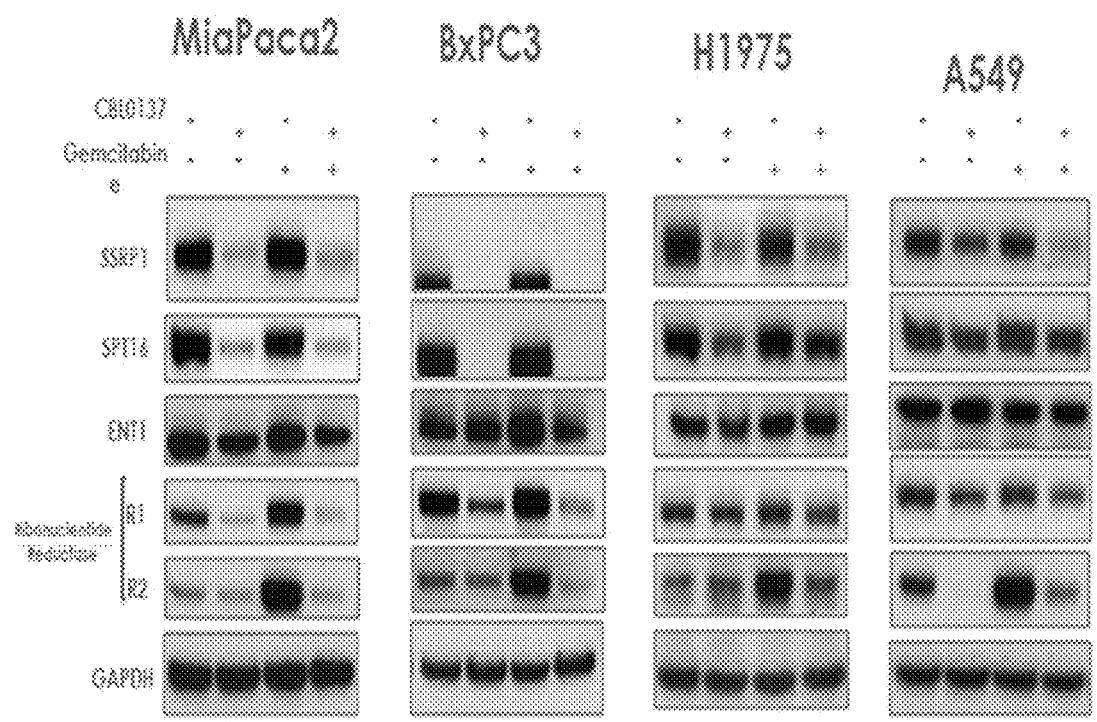

COMBINATION THERAPIES WITH CURAXINS

CROSS REFERENCE TO RELATED APPLICATIONS

This application claims priority to and the benefit of U.S. Provisional Application No. 61/975,865, filed on Apr. 6, 2014, and Patent Cooperation Treaty Application No. PCT/US2015/024514, filed on Apr. 6, 2014, the entire contents of each of which are incorporated herein by reference.

FIELD OF THE INVENTION

The present invention relates to, in part, methods and compositions for the treatment of various cancers, including treatments with CBL0137 and various combination agents.

BACKGROUND

A variety of cancer therapies are hindered by ineffectiveness against various tumors and, relatedly, problematic balancing of an effective dose and side effects. Indeed, it is common in cancer therapy for a treatment of various agents to be employed, particularly when a monotherapy provides disappointing clinical effects.

Therefore, further approaches for the treatment of various cancers that improve the clinical effectiveness of common cancer therapies are needed.

SUMMARY OF THE INVENTION

Accordingly, the present invention provides for compositions and methods that lead to more effective cancer therapy by increasing the effectiveness of various anti-cancer agents by, for example, improving a tumor reduction effect and/or reducing the side effects of a therapy by allowing for a reduction in dose without loss of therapeutic benefit. In various aspects, the present compositions and methods provide for synergistic effects that benefit the patient. In various aspects, the present compositions and methods allow for dose reduction without a loss in clinical effect, thereby reducing side effects and improving patient quality of life.

In some aspects, the present invention provides a method for treating cancer, comprising administering an effective amount of a composition of CBL0137 to a subject undergoing treatment with a kinase inhibitor or nucleoside analog chemotherapeutic agent. In some aspects, the present invention provides a method for treating cancer, comprising administering an effective amount of CBL0137 sequentially or simultaneously with administering an effective amount of a kinase inhibitor or nucleoside analog chemotherapeutic agent to a subject in need thereof. In other aspects, the present invention provides for compositions of, and anti-cancer uses of, co-formulations of CBL0137 and a kinase inhibitor or nucleoside analog chemotherapeutic agent. In further aspects, CBL0137 for use in treating, or in the manufacture of a medicament for the treatment of, various cancers with a kinase inhibitor or nucleoside analog chemotherapeutic agent is provided.

In various embodiments, the nucleoside analog chemotherapeutic agent is gemcitabine. In various embodiments, the kinase inhibitor chemotherapeutic agent is sorafenib.

In various embodiments, administration of CBL0137 and/or a kinase inhibitor or nucleoside analog chemotherapeutic agent allows for treatment of a subject with a sub-therapeutic dose of CBL0137 and/or a kinase inhibitor or nucleoside analog chemotherapeutic agent. In various embodiments, the combination of agents provides synergistic effects and/or reduces a subject's side effects from treatment. For example, in various embodiments, the use of, for example, CBL0137 and gemcitabine or/and sorafenib provides for more effective anti-cancer treatment (e.g. reduction in tumor growth) relative to any of the agents alone.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows mean fold-change in tumor volume in groups of Hep3B tumor-bearing nude mice. Panel A shows the mean fold-change in tumor volume (Hep3B study) of the tumor-bearing nude mice treated with vehicle or different regimens of CBL0137, sorafenib, or CBL0137+sorafenib. EOT represents end of treatment. Panel B shows the mean fold-change in tumor volume (Hep3B (sub-dose CBL0137) study) of the tumor-bearing nude mice treated with vehicle or different regimens of CBL0137, sorafenib, or CBL0137+sorafenib. Mean fold tumor growth was calculated by normalizing the tumor volume on Day X to that on Day 1 for each individual tumor (2 tumors per mouse) and then averaging the normalized values for all tumors in each group. For each group, data is presented for the time points at which there were a sufficient number of measurements to be representative of the group (i.e., measurements for ≥50% of the total number of animals in the group to prevent skewing of the data). Error bars represent the standard error of the means.

FIG. 6 shows the effect of CBL0137, sorafenib, or CBL0137+sorafenib treatment on the expression of NF-κB target genes for the HepG2 or Hep3B tumor-bearing nude mice. Specifically, Panels A and B correspond to the expression of IL-8 and TNF, respectively in HepG2 tumor-bearing nude mice after treatment with DMSO, CBL0137, sorafenib, CBL0137+sorafenib, DMSO+TNF, CBL0137+TNF, sorafenib+TNF, or CBL0137+sorafenib+TNF, Panels C and D correspond to the expression of IL-8 and TNF, respectively in Hep3B tumor-bearing nude mice after treatment with DMSO, CBL0137, sorafenib, CBL0137+sorafenib, DMSO+TNF, CBL0137+TNF, sorafenib+TNF, or CBL0137+sorafenib+TNF.

FIG. 11 shows Western blot analysis of CBL0137 and gemcitabine activity-related markers in MiaPaca2 and BXPC3 PDA and H1975 and A549 NSCLC cells in vitro. Specifically, Panel A corresponds to MiaPaca2 PDA, Panel B corresponds to BxPC3 FDA, Panel C corresponds to H1975 NSCLC, and Panel D corresponds to A549 NSCLC.

DETAILED DESCRIPTION OF THE INVENTION

Figure 1A:
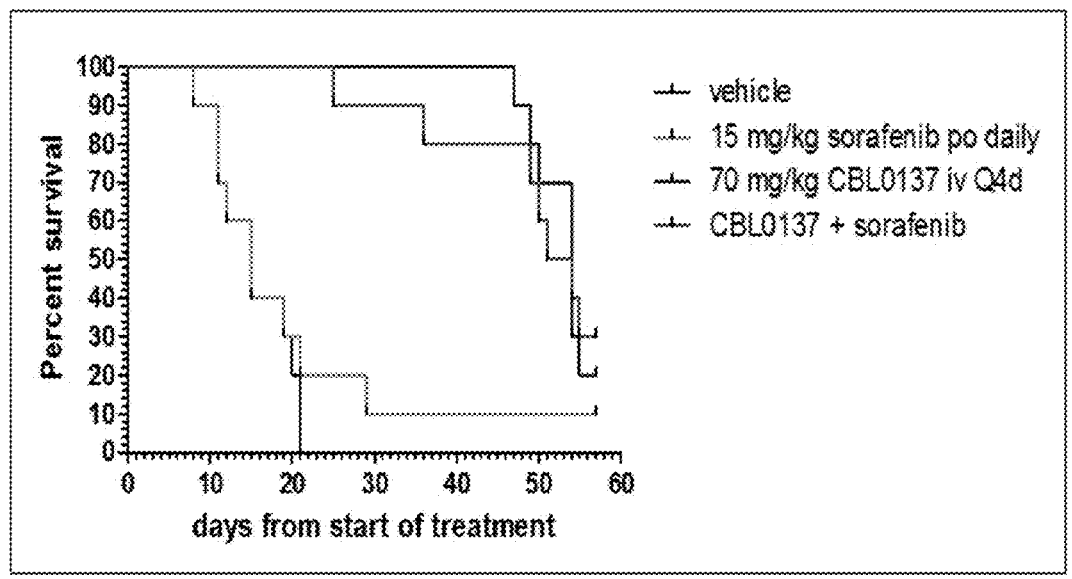
FIG. 1 shows Kaplan-Meier survival curves for groups of HepG2 tumor-bearing nude mice. Panel A shows the survival curve of the (HepG2 study) tumor-bearing nude mice treated with (labeled from left to right) vehicle (first line) or different regimens of CBL0137 (third line), sorafenib (second line), or CBL0137+sorafenib (fourth line). Panel B shows the survival curve of the (HepG2 (sub-dose CBL0137) study) tumor-bearing nude mice treated with (labeled from left to right) vehicle (first line) or different regimens of CBL0137 (second line), sorafenib (third line), or CBL0137+sorafenib (fourth line).

The present invention is based, in part, on the discovery of that CBL0137, can have synergistic effects when used in combination with various agents, including kinase inhibitors (e.g. sorafenib) or nucleoside analog chemotherapeutic agents (e.g. gemcitabine) and therefore expand the efficacy therapeutic window of these treatments (including allowing for administration of sub-therapeutic doses). Accordingly, the present invention provides improved methods of treating cancers.

In some aspects, the present invention provides a method for treating cancer, comprising administering an effective amount of CBL0137 to a subject undergoing treatment with a kinase inhibitor chemotherapeutic agent. In some aspects, the present invention provides a method for treating cancer, comprising administering an effective amount of CBL0137 sequentially or simultaneously with administering an effective amount of a kinase inhibitor chemotherapeutic agent to a subject in need thereof. In other aspects, the present invention provides for compositions of, and anti-cancer uses of, co-formulations of CBL0137 and a kinase inhibitor chemotherapeutic agent. In further aspects, provided are CBL0137 and a kinase inhibitor chemotherapeutic agent for use in treating, or in the manufacture of a medicament for the treatment of, various cancers.

CBL0137, also known as Curaxin-137, is described in International Patent Publication No. WO 2010/042445, the contents of which are hereby incorporated by reference in their entirety. CBL0137 is structurally represented as follows:

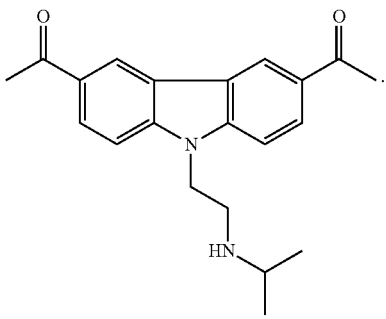 [SMILES: CC(=O)c1ccc2c(c1)c1cc(C(C)=O)ccc1n2CCNC(C)C]

In various embodiments, the kinase inhibitor chemotherapeutic agent inhibits one or more tyrosine protein kinases (e.g. VEGFR, PDGFR), Raf kinases (e.g. C-Raf, B-Raf), and intracellular serine/threonine kinases (e.g. C-Raf, wild-type B-Raf and mutant B-Rat). In various embodiments, the kinase inhibitor chemotherapeutic agent is anti-angiogenic. In various embodiments, the kinase inhibitor chemotherapeutic agent is selected from BI-2356, Sutent, PF-562271, AMG706, Dasatinib, Sorafenib, GSK461364A, Bez-235, and Lapatinib (see *Nature Reviews Cancer* 9, 28-39 (January 2009), the contents of which are hereby incorporated by reference). In a specific embodiment, the kinase inhibitor chemotherapeutic agent is sorafenib (e.g. NEXAVAR).

In various embodiments, CBL0137 when used in the context of a patient undergoing treatment with a kinase inhibitor chemotherapeutic agent (e.g. sorafenib) or when administered as a co-formulation or co-administration (e.g. sequentially or simultaneously) with a kinase inhibitor chemotherapeutic agent (e.g. sorafenib) increases the therapeutic window of the kinase inhibitor chemotherapeutic agent (e.g. sorafenib) and/or CBL0137.

For example, such administration may allow a sub-therapeutic dose of any of the agents to be administered, in various embodiments, the sub-therapeutic dose of CBL0137 and/or the kinase inhibitor chemotherapeutic agent is less than about 50%, or less than about 60%, or less than about 70%, or less than about 80%, or less than about 85%, or less than about 90% of an approved label dose and/or a maximum tolerated dose (MTD). In various embodiments, the use of a sub-therapeutic dose does not appreciably affect the extent of the therapeutic benefit of any of the agents or the combination of agents. For example, for sorafenib, treatment may comprise 400 mg twice daily and, in some embodiments, sub-therapeutic dose comprises about 400 mg daily, or about 480 mg daily, or about 560 mg daily, or about 640 mg daily, or about 680 mg daily, or about 720 mg daily. The present invention allows for daily or twice daily administration. In some embodiments, the present invention allows for a full dose to be taken daily and avoids the patient compliance problems of twice daily administration. Further, some patients require dose reduction of sorafenib because of side effects (e.g. reduction to 400 mg once daily, reduction to 400 mg every other day). In some embodiments, the present methods prevent the need for such dose reduction.

Further, in various embodiments; the CBL0137 when used in the context of a patient undergoing treatment with a kinase inhibitor chemotherapeutic agent (e.g. sorafenib) or when administered as a co-formulation or co-administration (e.g. sequentially or simultaneously) with a kinase inhibitor chemotherapeutic agent (e.g. sorafenib) allows for dose-reduction which accordingly provides for a reduction is side effects: For example, one or more of the following side effects of sorafenib may be reduced or eliminated: lymphopenia, hypophosphataemia, haemorrhage, hypertension, diarrhea, rash, alopecia, hand-foot syndrome, pruritus, erythema, increased amylase, increased lipase, fatigue, pain, nausea, vomiting, leucopoenia, neutropoenia, anaemia, thrombocytopenia, anorexia, weight loss, hypocalcaemia, hypokalaemia, depression, peripheral sensory neuropathy, tinnitus, congestive heart failure, myocardial infarction, myocardial ischaemia, hoarseness, constipation, stomatitis, dyspepsia, dysphagia, dry skin; exfoliative dermatitis; acne, skin desquamation, arthralgia, myalgia, renal failure, proteinuria, erectile dysfunction, asthenia, fever, and influenza-like illness.

In various embodiments, the increased therapeutic window of CBL0137 and/or the kinase inhibitor chemotherapeutic agent (e.g. sorafenib) comprises one or more of increasing a cancer patient's likelihood receiving CBL0137 and/or the kinase inhibitor chemotherapeutic agent (e.g. sorafenib) maintenance therapy; increasing a cancer patient's likelihood of receiving a complete regime of CBL0137 and/or the kinase inhibitor chemotherapeutic agent (e.g. sorafenib); increasing a cancer patient's likelihood of receiving more than a complete regime of CBL0137 and/or the kinase inhibitor chemotherapeutic agent (e.g. sorafenib); and increasing the dose or length of the CBL0137 and/or the kinase inhibitor chemotherapeutic agent (e.g. sorafenib) treatment.

In various embodiments, a combination of CBL0137 and the kinase inhibitor chemotherapeutic agent (e.g. sorafenib) produces a synergistic effect. In some embodiments, the synergistic effect is a tumor growth slowing effect, or a reduction of NF-κB genes; or a reduction or substantively complete abrogation of expression of one or more of TNF and IL-8.

In some embodiments, a variety of cancers (including primary or secondary tumors), as described herein may be treated with CBL0137 monotherapy (including, but not limited to, monotherapy in the context of a patient undergoing treatment with another agent, e.g. sorafenib) or combination therapy with a kinase inhibitor chemotherapeutic agent (e.g. sorafenib):

In some embodiments; the cancer is liver cancer. In some embodiments, the liver cancer is hepatocellular carcinoma (HOC).

In various embodiments; the liver cancer described herein is primary liver cancer. In various embodiments, the primary liver cancer is one of hepatocellular carcinoma (HCC), cholangiocarcinoma, angiosarcoma, and hepatoblastoma. In various embodiments, the present invention includes treatment of primary liver cancers that are related to one or more of the following risk factors of liver cancer cirrhosis, high alcohol consumption (including alcoholism), non-alcoholic fatty liver disease, infection with hepatitis viruses, smoking; low immunity, family history, diabetes, gallbladder removal, radiation from X-rays or CT scans, high body weight, betel quid consumption, and aflatoxin consumption.

In some embodiments, the liver cancer is a secondary liver cancer. In various embodiments, the secondary liver cancer is derived from one or more of the types of primary cancers that often metastasize to the liver, including, for example, colon, lung, stomach, pancreatic, breast cancers, biliary tract, esophageal, ovarian, prostate, kidney cancer, and melanoma.

In various embodiments, the liver cancer described herein has one or more of a liver cancer tissue marker, selected from, for example: GPC3; GPC3+heat shock protein 70+glutamine synthetase; Telomerase; Proliferating cell nuclear antigen labeling Index; Ki-67; MIB-1 E-cadherin, and β-catenin. In various embodiments, the liver cancer described herein has one or more of a liver cancer serum marker selected from, for example: AFP; AFP-concanavalin A; AFP-LCA binding; HCC-specific AFP band on isoelectric focusing (monosialylated AFP); AFP lectin-affinity subgroups (LCAreactive LCA-L3; erythroagglutinatingphytohemagglutinin-E4 reactive AFP-P4 and P5); Circulating free AFP-IgM complexes; DCP/prothrombin produced by vitamin K absence or antagonism II; Soluble NH2 fragment of GPC-3, a heparin sulfate proteoglycan; Golgi protein 73; Iso-yGTP; Ferritin; Variant alkaline phosphatase; al-Antitrypsin; al-Acid glycoprotein; Osteopontin; Aldolase A; 5[prime]-Nucleotide phosphodiesterase; CK13, CK19, TPA, TPS; Circulating free squamous cell carcinoma antigen-IgM complexes; α-Fucosyl-transferase; α-L-fucosidase; Transforming growth factor β1; Intercellular cell adhesion molecule 1; Anti-p53 antibody; Interleukin 8; Interleukin 6; Insulin-like growth factor II; Telomerase or telomerase reverse transcriptase mRNA; Vascular endothelial growth factor; Variant wild-type estrogen receptor; Vitamin B12-bindingprotein; Neurotensin; Free nucleic acids; Circulating cell-free serum DNA; Epigenetic abnormalities such as, for example, p16 hypermethylation; and Plasma proteasome.

In various embodiments, the liver cancer described herein has one or more of a liver cancer tumor cell marker selected from, for example: circulating tumor cells in peripheral blood detected by RTPCR of AFP mRNA. In various embodiments; the liver cancer described herein has one or more of a liver cancer genetic marker, selected from, for example: plasma glutamate carboxy-peptidase phospholipases A2 G13 and G7 and other cDNA microarray-derived encoded proteins; Melanoma antigen gene 1, 3; synovial sarcoma on X chromosome 1, 2, 4, 5; sarcoplasmic calcium-binding protein 1; New York esophageal squamous cell carcinoma 1; and Circulating methylated DNA (ras association domain family 1A).

In some embodiments, the liver cancer expresses alpha-fetoprotein. Further details of markers that define, in some embodiments, the liver cancers of the present invention are found at, for example, Sturgeon, et al. Use of Tumor Markers in Liver, Bladder, Cervical, and Gastric Cancers American Association for Clinical Chemistry; Inc. (2010), the contents of which are hereby incorporated by reference.

In various embodiments, the liver cancer described herein is classified as one or more of localized resectable, localized unresectable, advanced and recurrent. In various embodiments, the liver cancer described herein is classified with the AJCC (TNM) staging system, Stages are labeled using Roman numerals I through IV (1-4). Some stages are further sub-divided into A and B or even C. For the most part, the lower the number, the less the cancer has spread, A higher number, such as stage IV (4), means a more advanced cancer.

In various embodiments, the CBL0137 and/or kinase inhibitor chemotherapeutic agent is administered intravenously and/or orally.

In some aspects, the present invention provides a method for treating cancer, comprising administering an effective amount of CBL0137 to a subject undergoing treatment with a nucleoside analog chemotherapeutic agent. In some aspects, the present invention provides a method for treating cancer, comprising administering an effective amount of CBL0137 sequentially or simultaneously with administering an effective amount of a nucleoside analog chemotherapeutic agent to a subject in need thereof. In other aspects, the present invention provides for compositions of, and anti-cancer uses of, co-formulations of CBL0137 and a nucleoside analog chemotherapeutic agent. In further aspects, provided are CBL0137 and a nucleoside analog chemotherapeutic agent for use in treating, or in the manufacture of a medicament for the treatment of, various cancers.

In various embodiments, the nucleoside analog chemotherapeutic agent is selected from gemcitabine, capecitabine, 5-fluoruracil, 5'-deoxy-5-fluorouridine, BOF-A2, ftorafur, UFT, S-1, cytarabine, decitabine, cladribine, clofarabine, and fludarabine. In a specific embodiment, the nucleoside analog chemotherapeutic agent is gemcitabine (e.g. GEMZAR).

In various embodiments, CBL0137 when used in the context of a patient undergoing treatment with a nucleoside analog chemotherapeutic agent (e.g. gemcitabine) or when administered as a co-formulation or co-administration (e.g. sequentially or simultaneously) with a nucleoside analog chemotherapeutic agent (e.g. gemcitabine) increases the therapeutic window of the nucleoside analog chemotherapeutic agent (e.g. gemcitabine) and/or CBL0137. For example, such administration may allow a sub-therapeutic dose of any of the agents to be administered. In various embodiments, the sub-therapeutic dose of CBL0137 and/or the nucleoside analog chemotherapeutic agent (e.g. gemcitabine) is less than about 50%, or less than about 60%, or less than about 70%, or less than about 80%, or less than about 85%, or less than about 90% of an approved label dose and/or a maximum tolerated dose (MTD). In various embodiments, the use of a sub-therapeutic dose does not appreciably affect the extent of the therapeutic benefit of any of the agents or the combination of agents. For example, for gemcitabine, treatment may comprise about 1-1.2 $g/m^2$ of body surface area and, in some embodiments, sub-therapeutic dose comprises about 0.5-0.6 $g/m^2$, or about 0.64-0.72 $g/m^2$, or about 0.7-0.84 $g/m^2$ or about 0.8-0.96 $g/m^2$, or about 0.85-1.02 $g/m^2$, or about 0.9-1.08 $g/m^2$.

Further, in various embodiments, the CBL0137 when used in the context of a patient undergoing treatment with a nucleoside analog chemotherapeutic agent (e.g. gemcitabine) or when administered as a co-formulation or co-administration (e.g. sequentially or simultaneously) with a nucleoside analog chemotherapeutic agent (e.g. gemcitabine) allows for dose reduction which accordingly provides for a reduction in side effects. For example, one or more of the following side effects of gemcitabine may be reduced or eliminated; flu-like symptoms (e.g. muscle pain, fever, headache, chills, and fatigue), fever (e.g. within 6-12 hours of first dose), fatigue, nausea, vomiting, poor appetite, skin rash, allergic reaction, diarrhea, weakness, hair loss, mouth sores, difficulty sleeping, and shortness of breath).

In various embodiments, the increased therapeutic window of CBL0137 and/or the nucleoside analog chemotherapeutic agent (e.g. gemcitabine) comprises one or more of increasing a cancer patient's likelihood receiving CBL0137 and/or the nucleoside analog chemotherapeutic agent (e.g. gemcitabine) maintenance therapy; increasing a cancer patient's likelihood of receiving a complete regime of CBL0137 and/or the nucleoside analog chemotherapeutic agent (e.g. gemcitabine); increasing a cancer patient's likelihood of receiving more than a complete regime of CBL0137 and/or the nucleoside analog chemotherapeutic agent (e.g. gemcitabine); and increasing the dose or length of the CBL0137 and/or the nucleoside analog chemotherapeutic agent (e.g. gemcitabine) treatment.

For example, a common gemcitabine regimen for pancreatic cancer is injection (e.g. IV over a period of 30 minutes) once a week for up to 7 weeks to start, then a week without treatment. After that, the dose is once a week for 3 weeks followed by a week off. Often about four cycles are used.

In some embodiments, the treatment recommendations for adjuvant chemotherapy and chemoradiation for pancreatic cancer is gemcitabine 1000 mg/m$^2$ IV over 30 minutes weekly for 3 weeks or concurrent chemoradiation starting 1-2 weeks after gemcitabine; 5-fluorouracil (FU) 250 mg/m$^2$/day continuous IV infusion via pump during radiation; or radiotherapy 1.8 Gy/day to a total of 50.4 Gy; then 3-5 weeks after chemoradiation: gemcitabine 1000 mg/m$^2$ IV over 30 minutes weekly; every 28 day for 3 cycles. The above regimens may be preceded by capecitabine 800-900 mg/m$^2$ PO BID plus radiation for 5-6 weeks.

In some embodiments, the treatment recommendations for locally advanced, unresectable disease is neoadjuvant therapy: gemcitabine 1000 mg/m$^2$ IV over 30 minutes weekly for 3 weeks; every 28 days and/or 5-FU 500 mg/m$^2$/day IV bolus on days 1-3 and 29-31 with concurrent radiotherapy 40 Gy.

In some embodiments, the treatment recommendations for metastatic disease paclitaxel protein bound 125 mg/m$^2$ plus gemcitabine 1000 mg/m$^2$ IV over 30-40 minutes on days 1, 8, and 15 of each 28-day cycle, or gemcitabine 1000 mg/m$^2$ IV over 30 minutes weekly for 7 weeks, followed by 1 week off, then weekly for 3 weeks; every 28 days, or gemcitabine 1000 mg/m$^2$ IV over 30 minutes on days 1 and 15 plus cisplatin 50 mg/m$^2$ IV over 1 hour on days 1 and 15; every 28 days, or gemcitabine 1000 mg/m$^2$ IV weekly for 7 week plus erlotinib 100 mg PO daily on Days 1-56, followed by 1 week off; then gemcitabine 1000 mg/m$^2$ IV on days 1, 8, and 15 every 28 d plus erlotinib 100 mg PO daily on Days 1-28 for up to 4 cycles, or gemcitabine 1000 mg/m$^2$ IV weekly for 3 week; every 28 d; plus capecitabine 1660 mg/m$^2$/day weekly for 3 week; every 28 d.

The present methods may open the therapeutic window such that the full regiment can be competed, or the dose increased, the periods without treatment shortened or eliminated, or the number of cycles reduced or increased. Further, CBL0137 may supplement or supplant any of the agents in the regimens described herein.

For lung cancer a common gemcitabine regimen is injection (e.g. IV for a period of 30 minutes) for 3 weeks with 1 week off. An acceptable chemotherapy regimens for adjuvant chemotherapy for stage I or II (goal to complete 4 cycles) for non-small cell lung cancer is cisplatin 75 mg/m$^2$ IV on day 1 plus gemcitabine 1250 mg/m$^2$ on days 1 and 8 every 21 days. Additionally, oxaliplatin with gemcitabine (Gem/Ox) may be used.

The present methods may open the therapeutic window such that the full regiment can be competed, or the dose increased, the periods without treatment shortened or eliminated, or the number of cycles reduced or increased. Further, CBL0137 may supplement or supplant any of the agents in the regimens described herein.

In various embodiments, a combination of CBL0137 and the nucleoside analog chemotherapeutic agent produces a synergistic effect. In some embodiments, the effect is a synergistic tumor growth slowing effect. In some embodiments (e.g. in the treatment of pancreatic or lung cancer), CBL0137 produces a reduction of genes controlling gemcitabine sensitivity/resistance, e.g. a reduction of one or more of cytadine deaminase and ribonucleotide reductase subunits.

In some embodiments, a variety of cancers (including primary or secondary tumors), as described herein may be treated with CBL0137 monotherapy (including but not limited to monotherapy in the context of a patient undergoing treatment with another agent (e.g. gemcitabine) or combination therapy with a nucleoside analog chemotherapeutic agent (e.g. gemcitabine).

In some embodiments, the cancer is pancreatic cancer. In some embodiments, the pancreatic cancer is pancreatic ductal adenocarcinoma (PDAC).

In some embodiments, the pancreatic cancer is an exocrine pancreas cancer. For example, the cancer may a ductal adenocarcinoma and optionally may be characterized by moderately to poorly differentiated glandular structures on microscopic examination. The etiology of the cancer may be, for example, one or more of KRAS mutations, CDKN2A mutations/deletions, TP53 mutations, SMAD4 deletions/mutations, and SWI/SNF mutations/deletions. The cancer may comprise one of more precancerous lesions (e.g. pancreatic intraepithelial neoplasia, intraductal papillary mucinous neoplasms, and mucinous cystic neoplasms). The exocrine pancreas cancer may also be mucinous, adenosquamous carcinomas, signet ring cell carcinomas, hepatoid carcinomas, colloid carcinomas, undifferentiated carcinomas, and undifferentiated carcinomas with osteoclast-like giant cells.

Further, the invention provides for pancreatic cystic neoplasms and pancreatic neuroendocrine tumors (e.g. pancreas endocrine tumors (PETs), and pancreatic neuroendocrine tumors (PNETs)) and pancreatic neuroendocrine carcinomas (PNEC).

In some embodiments, the cancer is lung cancer. In some embodiments, the lung cancer is non-small cell lung cancer.

Lung cancers are broadly classified into two types: small cell lung cancers (SCLC) and non-small cell lung cancers (NSCLC), based upon the microscopic appearance of the tumor cells. SCLC is aggressive and rapidly growing and strongly related to cigarette smoking. SCLCs metastasize rapidly to many sites within the body and are most often discovered after they have spread extensively. NSCLC is the most common lung cancer and has three main types designated by the type of cells found in the tumor: adenocarcinomas, squamous cell carcinomas and large cell carcinomas. Also provided are bronchial carcinoids.

In various embodiments, the CBL0137 and/or the nucleoside analog chemotherapeutic agent is administered intravenously and/or orally.

In various embodiments, the present agents are useful as adjuvant therapies. Adjuvant therapy is treatment that is given in addition to a primary or main treatment. In various embodiments, a patient is undergoing one or more primary or main treatments. CBL0137 (and/or additional agents, such as kinase inhibitor chemotherapeutic agents, e.g. sorafenib and/or nucleoside analog chemotherapeutic agents (e.g. gemcitabine)) may be administered in conjunction with a primary or main treatment. For example, CBL0137 (and/or additional agents, such as kinase inhibitor chemotherapeutic agents, e.g. sorafenib and/or nucleoside analog chemotherapeutic agents (e.g. gemcitabine)) may be adjuvant to resection of the primary tumor(s).

Also, in various embodiments, the present agents are useful as neoadjuvant therapies. Neoadjuvant therapy refers to therapy that is given to before primary or main treatment, often to prepare a patient for the primary or main treatment. For example, in some embodiments, treatment with the present agents will lessen the severity of the disease and make it more amenable to a primary or main treatment. In a specific embodiment, CBL0137 (and/or additional agents, such as kinase inhibitor chemotherapeutic agents, e.g. sorafenib and/or nucleoside analog chemotherapeutic agents (e.g. gemcitabine)) are used in treating a patient to allow for subsequent resection (e.g. surgical resection).

In various embodiments, additional combination agents are also provided and include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethyienimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chiornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omega (see, e.g., Agnew, Chem. Intl. Ed. Engl., 33; 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine; thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatrexate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Crerrophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; 6-thioguanine; mercaptopurine; methotrexate; platinum analogs such as cisplatin, oxaliplatin and carboplatin; vinblastine; platinum; etoposide (VP-16); Ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin; including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

As mentioned above, in various embodiments, the present invention pertains to cancers and/or tumors; for example, the treatment or prevention of cancers and/or tumors. As used herein, "cancer" or "tumor" refers to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g. virus infected cells). A subject that has a cancer or a tumor is a subject having objectively measurable cancer cells present in the subject's body. Cancers which migrate from their original location and seed vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. "Metastasis" refers to the spread of cancer from a primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases may be detected through the sole or combined use of magnetic resonance imaging (MRI) scans, computed tomography (CT) scans, blood and platelet counts, liver function studies, chest X-rays and bone scans in addition to the monitoring of specific symptoms.

The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be lymphoma.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the CBL0137 (and/or additional agents, such as kinase inhibitor chemotherapeutic agents, e.g. sorafenib and/or nucleoside analog chemotherapeutic agents (e.g. gemcitabine)) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

In still other embodiments, the CBL0137 (and/or additional agents, such as kinase inhibitor chemotherapeutic agents, e.g. sorafenib and/or nucleoside analog chemotherapeutic agents (c.a. gemcitabine)) described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The f the CBL0137 (and/or additional agents, such as kinase inhibitor chemotherapeutic agents, e.g. sorafenib and/or nucleoside analog chemotherapeutic agents (e.g. gemcitabine)) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, di nitrobenzoate, hydroxybenzoate, methoxybenzoate, methylbenzoate, o-acetoxybenzoate, naphthalene-2-benzoate, isobutyrate, phenylbutyrate, a-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthaiene-1,5-sulfonate, xylenesulfonate, and tartrate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine, tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any the CBL0137 (and/or additional agents, such as kinase inhibitor chemotherapeutic agents, e.g. sorafenib and/or nucleoside analog chemotherapeutic agents (e.g. gemcitabine)) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The present invention includes the CBL0137 (and/or additional agents, such as kinase inhibitor chemotherapeutic agents, e.g. sorafenib and/or nucleoside analog chemotherapeutic agents (e.g. gemcitabine)) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155), Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the CBL0137 (and/or additional agents, such as kinase inhibitor chemotherapeutic agents, e.g. sorafenib and/or nucleoside analog chemotherapeutic agents (e.g. gemcitabine)) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the CBL0137 (and/or additional agents, such as kinase inhibitor chemotherapeutic agents, e.g. sorafenib and/or nucleoside analog chemotherapeutic agents (e.g. gemcitabine)) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any the CBL0137 (and/or additional agents, such as kinase inhibitor chemotherapeutic agents, e.g. sorafenib and/or nucleoside analog chemotherapeutic agents (e.g. gemcitabine)) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and depends in-part upon the site of the medical condition. In most instances, administration results in the release of any agent described herein into the bloodstream.

The CBL0137 (and/or additional agents, such as kinase inhibitor chemotherapeutic agents, e.g. sorafenib and/or nucleoside analog chemotherapeutic agents (e.g. gemcitabine)) described herein can be administered orally. Such CBL0137 (and/or additional agents, such as kinase inhibitor chemotherapeutic agents, e.g. sorafenib and/or nucleoside analog chemotherapeutic agents (e.g. gemcitabine)) can also be administered by any other convenient route, for example, by intravenous infusion or bolus injection epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment.

In one embodiment, CBL0137 (and/or additional agents, such as kinase inhibitor chemotherapeutic agents, e.g. sorafenib and/or nucleoside analog chemotherapeutic agents (e.g. gemcitabine)) described herein is formulated in accordance with routine procedures as a composition adapted for oral administration to humans. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving CBL0137 (and/or additional agents, such as kinase inhibitor chemotherapeutic agents, e.g. sorafenib and/or nucleoside analog chemotherapeutic agents (e.g. gemcitabine)) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use, They may contain, for example, suspending or dispersing agents known in the art.

The dosage of CBL0137 (and/or additional agents, such as kinase inhibitor chemotherapeutic agents, e.g. sorafenib and/or nucleoside analog chemotherapeutic agents (e.g. gemcitabine)) described herein as well as the dosing schedule can depend on various parameters, including, but not limited to, the disease being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

The amount of a CBL0137 (and/or additional agents, such as kinase inhibitor chemotherapeutic agents, e.g. sorafenib and/or nucleoside analog chemotherapeutic agents (e.g. gemcitabine)) described herein that is admixed with the carrier materials to produce a single dosage can vary depending upon the subject being treated and the particular mode of administration. In vitro or in vivo assays can be employed to help identify optimal dosage ranges.

In general, the doses that are useful are known to those in the art. For example, doses may be determined with reference *Physicians' Desk Reference,* 66th Edition, PDR Network; 2012 Edition (Dec. 27, 2011), the contents of which are incorporated by reference in its entirety. In some embodiments, the present invention allows a patient to receive doses that exceed those determined with reference *Physicians' Desk Reference* or doses that are below the approved label amount or MTD.

The dosage of CBL0137 (and/or additional agents, such as kinase inhibitor chemotherapeutic agents, e.g. sorafenib and/or nucleoside analog chemotherapeutic agents (e.g. gemcitabine)) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

In some embodiments, when orally administered to a mammal, the dosage of CBL0137 (and/or additional agents, such as kinase inhibitor chemotherapeutic agents, e.g. sorafenib and/or nucleoside analog chemotherapeutic agents (e.g. gemcitabine)) described herein may be 0.001 mg/kg/day to 100 mg/kg/day, 0.01 mg/kg/day to 50 mg/kg/day, or 0.1 mg/kg/day to 10 mg/kg/day. When orally administered to a human, the dosage of any agent described herein is normally 0.001 mg to 1000 mg per day, 1 mg to 600 mg per day, or 5 mg to 30 mg per day.

In some embodiments, for administration of CBL0137 (and/or additional agents, such as kinase inhibitor chemotherapeutic agents, e.g. sorafenib and/or nucleoside analog chemotherapeutic agents (e.g. gemcitabine)) described herein by parenteral injection, the dosage may be 0.1 mg to 250 mg per day, 1 mg to 20 mg per day, or 3 mg to 5 mg per day. Injections may be given up to four times daily. Generally, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

In another embodiment, delivery can be in a vesicle, in particular a liposome (see Langer, 1990, *Science* 249:1527-1533; Treat et al., in *Liposomes in the Therapy of Infectious Disease and Cancer,* Lopez-Berestein and Fidler (eds.), Liss, New York, pp. 353-365 (1989).

CBL0137 (and/or additional agents, such as kinase inhibitor chemotherapeutic agents, e.g. sorafenib and/or nucleoside analog chemotherapeutic agents (e.g. gemcitabine)) can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein; can be readily selected for use with the active ingredients of the agents described herein. The invention thus provides single unit dosage forms suitable for oral administration such as, but not limited to, tablets, capsules; gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of CBL0137 (and/or additional agents, such as kinase inhibitor chemotherapeutic agents, e.g. sorafenib and/or nucleoside analog chemotherapeutic agents (e.g. gemcitabine)) described herein can; independently, be one to four times daily or one to four times per month or one to six times per year or once every two, three, four or five years. Administration can be for the duration of one day or one month, two months, three months, six months, one year, two years, three years, and may even be for the life of the subject. Chronic, long-term administration may be indicated. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing CBL0137 (and/or additional agents, such as kinase inhibitor chemotherapeutic agents, e.g. sorafenib and/or nucleoside analog chemotherapeutic agents (e.g. gemcitabine)) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. CBL0137 (and/or additional agents, such as kinase inhibitor chemotherapeutic agents, e.g. sorafenib and/or nucleoside analog chemotherapeutic agents (e.g. gemcitabine)) described herein can be administered in a single daily dose, or the total daily dosage can be administered in divided doses of two, three or four times daily. Furthermore, CBL0137 (and/or additional agents, such as kinase inhibitor chemotherapeutic agents, e.g. sorafenib and/or nucleoside analog chemotherapeutic agents (e.g. gemcitabine)) described herein can be administered continuously rather than intermittently throughout the dosage regimen.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

The invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein. In one embodiment, the kit comprises CBL0137 and a kinase inhibitor chemotherapeutic agent, e.g. sorafenib and/or a nucleoside analog chemotherapeutic agent, e.g. gemcitabine.

This invention is further illustrated by the following non-limiting examples.

EXAMPLES

Materials and Methods

Animals: Forty female athymic nude mice were obtained for each Hepatocellular Carcinoma (HOC) study (HepG2, HepG2 (sub-dose CBL0137), Hep3B, and Hep3B (sub-dose CBL0137) and split into treatment groups consisting of 10 animals per group (2 cages of 5 mice per cage). For the HepG2 (sub-dose CBL0137) study, the vehicle-treated control Group 1, consisted of 9 animals (1 cage of 5 mice and 1 cage of 4 mice). Fifty female SCID mice were obtained from LAR of Roswell Park Cancer Institute for each Pancreatic cancer study and split into treatment groups consisting of 5 animals (housed in one cage) per group. Seventy and sixty female athymic nude mice were obtained for each H1975 Non-Small Cell Lung Cancer Xenograft study and split into treatment groups consisting of 10 animals per group (2 cages of 5 mice per cage).

Tumors: HepG2 HCC tumor pieces were supplied by Technical Staff of Animal Group, BBL (80 pieces). Hep3B HCC tumor pieces were supplied by Technical Staff of Animal Research Core, BBL (80 pieces). PDA #13590 and #13756 tumor pieces were supplied by Technical Staff of Animal Research Core, BBL (100 pieces). H1975 and A549 NSCLC tumor cells were supplied by Technical Staff of BBL (8-9 mL at $5 \times 10^7$ cells/ml).

Description of HepG2 test material: 2 mm×2 mm pieces of non-necrotic HepG2 tumors (passage 2 tumors, ~600-700 mm$^3$ at the time of harvest (HepG2 study); passage 1 tumors, ~500-900 mm$^3$ at the time of harvest (HepG2 (sub-dose CBL0137) study) propagated in nude mice, originally from human HepG2 hepatocellular carcinoma cells (ATCC).

Description of Hep3B test material: 2 mm×2 mm pieces of non-necrotic Hep3B tumors (passage 1 tumors, ~600-700 mm$^3$ at the time of harvest (Hep3B study); passage 9 tumors, ~800 mm$^3$ at the time of harvest (Hep3B (sub-dose CBL0137) study) propagated in nude mice, originally from human Hep3B hepatocellular carcinoma cells (ATCC).

Description of PDA test material: 2 mm×2 mm pieces of non-necrotic patient-derived PDA #13590 or #13756 tumors (passage 6 tumors, ~600-700 mm$^3$ at the time of harvest) propagated in SCID mice.

Description of H1975 NSCLS test material: Human H1975 NSCLC cell line (originally from ATCC) suspension was mixed 1:1 with Matrigel at 5×107 cells/ml (5×10$^6$ cells delivered per 100 µl injection) and kept on ice until inoculation.

All tumors pieces were freshly harvested, aseptically handled in a biosafety cabinet, and placed in sterile RPMI+ 10% FBS medium or D-PBS prior to implantation into mice. Pieces were implanted immediately after harvesting.

Reagents and Drugs: Captisol, supplied by Cydex (Catalog no.—Captisol; Batch—NC-04A-05033; and Storage Conditions—2-5° C.); D-PBS without calcium chloride or magnesium chloride, 1×, supplied by Media Core, Cleveland Clinic Foundation (CCF) (Catalog no.—121-500p and Storage Conditions—2-5° C., kept on ice during use); CBL0137, supplied by Aptuit (Catalog no.—CBL0137; Batch—10-106-88-30; and Storage Conditions—Room temperature in a desiccators); Gemcitabine, hydrochloride salt, supplied by LC Laboratories (Catalog no.—G-4177; Batch—GMC-103; and Storage Conditions—−20° C.); Sorafenib, supplied by LC Laboratories (Catalog no.—S-8502; Batch—BSF-105; and Storage Conditions—−20° C.); RPMI1640 supplied by Media Core, CCF (Catalog no.—CCF, 12-500p and Storage Conditions—4° C., kept on ice during use); Fetal Bovine Serum (FBS), supplied by Atlanta Biologicals (Catalog no.—S11050; Batch—A1031; Storage Conditions—−20° C.); Sodium chloride (NaCl, 0.9% for injection), supplied by Baxter Healthcare Corp. or Hospira, Inc. (Batch—P220525 (Baxter) or 64-106-JT (Hospira) and Storage Conditions—room temperature); Matrigel, supplied by Fisher Scientific (Catalog no.—CB354248 (BD 12483); Batch—37399; and Storage Conditions—−20° C.); and Dimethylsulfoxide (DMSO), supplied by Sigma-Aldrich (Catalog no.—34869-100 ml; Batch—SHBB7695V; and Storage Conditions—Room temperature).

Preparation of Drugs and Reagents: Dosing solutions were prepared in four lots for the HCC and PDA studies (one for each week of the treatment phase of the study) to ensure that fresh solutions were used throughout the study. On each solution preparation date for the HepG2 study, 35 ml of Sorafenib at 1.9 mg/ml was made up in 5% DMSO-200 mg/ml Captisol and 12 ml of CBL0137 at 8.8 mg/ml was made up in 100 mg/ml Captisol. All dosing solutions of drugs and vehicle control solutions (100 mg/ml Captisol and 5% DMSO-200 mg/ml Captisol) were filter-sterilized.

For the HepG2 (sub-dose CBL0137) study, 36 ml of sorafenib at 3.75 mg/ml was made up in 5% DMSO-200 mg/ml Captisol and 13 ml of CBL0137 at 7.5 mg/ml was made up in 100 mg/ml Captisol. Solutions for iv administration (dosing solutions of CBL0137 and the 100 mg/ml Captisol vehicle control solution) were filter-sterilized.

For the Hep3B study, 34.2 ml of Sorafenib at 3.75 mg/ml was made up in 5% DMSO-200 mg/ml Captisol and 14 ml of CBL0137 at 7.5 mg/ml was made up in 100 mg/ml Captisol. Solutions for iv administration (dosing solutions of CBL0137 and the 100 mg/ml Captisol vehicle control solution) were filter-sterilized.

For the Hep3B (sub-dose CBL0137) study, dosing solutions were prepared in two lots (one each for two weeks of the treatment phase of the study). For the first two weeks of dosing, 14 ml of CBL0137 at 6.25 mg/ml was made up in 100 mg/ml Captisol and 68.4 ml of sorafenib at 3.75 mg/ml was made up in 5% DMSO-200 mg/ml Captisol. For the last two weeks of dosing, 14 ml of CBL0137 at 6.25 mg/ml was made up in 100 mg/ml Captisol and 68.4 ml of sorafenib at 3.75 mg/ml was made up in 5% DMSO-200 mg/ml Captisol.

For the PDA studies, the solutions of gemcitabine and CBL0137 were prepared as 12 ml of gemcitabine at 5.0 mg/ml made up in Milli-Q water and 7 ml of CBL0137 at 10.0 mg/ml made up in 150 mg/ml Captisol and were filter-sterilized.

All of the above prepared solutions were stored at 4° C. during the week of their use.

For the NSCLC studies, solutions were prepared in two lots (once per 2 weeks) to ensure that fresh solutions were used throughout the study. For H1975 NSCLC Study 1, the solutions were two tubes of 10 ml each at 4.4 mg/ml and 8.8 mg/ml CBL0137 in 100 mg/ml Captisol and two tubes of 10 ml each at 5.0 mg/ml and 2.5 mg/ml gemcitabine in sterile water. For H1975 NSCLC Study 2, the solutions were one tube of 16 ml at 11.25 mg/ml CBL0137 in 150 mg/ml Captisol and two tubes of 25 ml each at 1.0 mg/ml gemcitabine in sterile water.

Preparation and subcutaneous implantation of tumor pieces: HepG2 tumors (passage 2 for HepG2 study and passage 1 for HepG2 (sub-dose CLB0137) study) or Hep3B tumors (passage 1 for Hep3B study and passage 9 for Hep3B (sub-dose CLB0137) study) were propagated in athymic nude mice and harvested from euthanized mice when they reached ~500-900 mm$^3$. PDA tumors (passage 6) were propagated in SCID mice (both flanks) and harvested from euthanized mice when they reached ~600-700 mm$^3$ in size. Harvested tumors were transferred to a sterile Petri dish containing RPMI-10% FBS medium or D-PBS plus penicillin/streptomycin. Enough media was added to bathe the tumor in order to ensure the viability of the transplant material. Tumors were dissected into 2 mm×2 mm cubes using a sterile scalpel. Care was taken to make the pieces as uniform in size and shape as possible. Tumor pieces were implanted into recipient mice immediately after being prepared.

Preparation and inoculation of tumor cells: The night before inoculation, the Matrigel was placed on ice in the refrigerator to thaw. Prior to the start of cell harvesting, a supply of pipettes, tubes and tips were placed into the freezer so that they were cold when it was time to work with the Matrigel. One ml syringes and ½" 23 G needles were also pre-chilled. This step was necessary to prevent premature solidification of Matrigel, which becomes solid at room temperature or higher (i.e., 37° C.).

H1975 cell suspension was prepared immediately before tumor inoculation in PBS. H1975 cells at passage 16 were harvested from forty 150 mm diameter dishes and diluted to 10×10$^7$ cells/ml in PBS (5.87 ml). Just prior to inoculation, using pre-chilled tips and tubes, 4.5 ml of this cell suspension was mixed with an equal volume of Matrigel (1:1) to a total volume of 9 mL Cell suspensions were kept on ice. The final concentration of cells was 5×cells/ml.

Prior to inoculation of mice, the tumor cell-Matrigel mixture was carefully mixed by inverting the tube several times. A pre-chilled 1 nil syringe was filled with tumor cell-Matrigel mixture and then a pre-chilled ½" 23 G capped needle was attached to the end of syringe to perform the injection. The closed filled syringe was inverted several times and then 100 µl of the cell-Matrigel mixture was inoculated subcutaneously into the left flank of each mouse.

For inoculation, mice were anesthetized with isoflurane (3-4% induction in 100% O$_2$, 1-2% maintenance) to aid in proper subcutaneous inoculation.

Tumor Size Measurements: Tumor size was measured by digital caliper in two dimensions (in mm): maximum length (l) and maximum width (w) taken perpendicular to one another. The measurements were used to calculate tumor volume according to the formula: tumor volume=(l×w2)/2 (w<l). The value obtained by this formula is also equal to the mass of the tumor in mg. Starting 2 days after tumor implantation, tumor measurements were made every 2-3 days prior to treatment initiation and then twice per week (e.g., on Day 1 (D1, the day of treatment initiation), D4, D8, D11, D15, D18, D22, D25, D29, D32, D36, D39, D43, D46, D50, D53 and D57). Tumor measurements were collected more frequently when tumor size approached the tumor size endpoint in order to prevent passing the endpoint between scheduled measurements.

Administration of test and control articles: Mice were administered the designated solutions when the mean tumor volume per treatment group was ~45-200 mm$^3$.

Mice of the HepG2 study were treated with CBL0137 and/or sorafenib according to the following regimens: 1) vehicle; 2) 15 mg/kg sorafenib orally (po) daily; 3) 70 mg/kg CBL0137 intravenously every 4th day (Q4 d); or 4) 70 mg/kg CBL0137 iv Q4 d+15 mg/kg sorafenib po daily. Mice of the HepG2 (sub-dose CBL0137) study were treated with: 1) vehicle control; 2) 30 mg/kg sorafenib orally (po) daily; 3) 60 mg/kg CBL0137 intravenously (iv) every 4th day (Q4 d); or 4) 60 mg/kg CBL0137 iv Q4 d+30 mg/kg sorafenib po daily. Mice of the Hep3B study were treated with: 1) vehicle, 2) 30 mg/kg sorafenib po daily, 3) 60 mg/kg CBL0137 iv Q4 d, or 4) 60 mg/kg CBL0137 iv Q4 d+30 mg/kg sorafenib po daily. Mice of the Hep3B (sub-dose CBL0137) study were treated with: 1) vehicle; 2) 30 mg/kg sorafenib orally (po) daily; 3) 50 mg/kg CBL0137 intravenously (iv) every 4th day (Q4 d); or 4) 50 mg/kg CBL0137 iv Q4 d+30 mg/kg sorafenib po daily. The negative control group (Group 1) was treated for 4 weeks with a combination of the vehicles used for delivery of CBL0137 (100 mg/ml Captisol) and sorafenib (5% DMSO-200 mg/ml Captisol) using the same delivery route and schedule as the corresponding drug. Q4 d dosing with CBL0137 was performed on D1, D5, D9, D13, D17, D21, D25, and D29 of the study and daily dosing with sorafenib was performed on D1-D28. For groups that received only one drug (either CBL0137 or sorafenib) rather than both, the vehicle for the drug that was not given was administered in its place as a mock administration using the corresponding delivery route and schedule. The volume of the dosing solution administered orally or intravenously was 8 ml/kg of body weight, Intravenous injections were performed via the tail vein. Administration of drugs was done slowly without force on the syringe.

Mice of the PDA study were treated with CBL0137 and/or gemcitabine according to the following regimens: 1) vehicle; 2) 40 mg/kg gemcitabine ip Q4 d for 4 weeks; 3) 90 mg/kg CBL0137 iv 1×/wk for 4 weeks; or 4) 40 mg/kg gemcitabine ip Q4 d for 4 weeks+90 mg/kg CBL0137 iv 1×/wk for 4 weeks. Mice of the PDA #13756 study were treated with CBL0137 and/or gemcitabine according to the following regimens: 1) vehicle; 2) 40 mg/kg gemcitabine ip Q4 d for 4 weeks; 3) 80 mg/kg CBL0137 iv 1×/wk for 4 weeks; or 4) 40 mg/kg gemcitabine ip Q4 d for 4 weeks+80 mg/kg CBL0137 iv 1×/wk for 4 weeks. Q4 d dosing with gemcitabine was performed on D1, D5, D9, D13, D17, D21, D25, and D29 of the study and 1×/wk dosing with CBL0137 was performed on D1, D8, D15 and D22. The negative control group (Group 1) was treated for 4 weeks with a combination of the vehicles used for delivery of gemcitabine (sterile MilliQ water) and CBL0137 (150 mg/ml Captisol) using the same delivery route and schedule as the corresponding drug. The volume of dosing solution administered ip or iv was 8 ml/kg mouse body weight. Intravenous injections were performed via the tail vein. Administration of drugs was done slowly without force on the syringe.

Mice of the NSCLC Study 1 were treated with CBL0137 and/or gemcitabine according to the following regimens: 1) vehicle; 2) 70 mg/kg CBL0137 iv Q4 d; 3) 40 mg/kg gemcitabine ip Q4 d; or 4) 70 mg/kg CBL0137 iv Q4 d+40 mg/kg gemcitabine ip Q4 d. Mice of the NSCLC Study 2 were treated with CBL0137 and/or gemcitabine according to the following regimens: 1) vehicle; 2) 90 mg/kg CBL0137 iv 1/wk for 4 weeks; 3) 20 mg/kg gemcitabine ip Q4 d for 4 weeks; or 4) 90 mg/kg CBL0137 iv 1/wk for 4 weeks+20 mg/kg gemcitabine ip Q4 d for 4 weeks. For all groups, Q4 d dosing was performed on D1, 05, 09, 013, 017, 021, 025, and 029 of the study. For groups that received only one drug rather than both, the vehicle for the drug that was not given was administered in its place as a mock administration. The volume of dosing solution administered ip or iv was 8 ml/kg mouse body weight. Intravenous injections were performed via the tail vein. Administration of drugs was done slowly without force on the syringe.

Monitoring and Sample Collection: Twice daily, mice were monitored for mortality and morbidity for the duration of the experiment. In particular, mice were observed for changes in skin, fur, motor activity, and major general behavior patterns. All abnormal observations were documented and semi-quantitative scores were assigned for "body condition," "posture," and "activity." Scores of 4, 3, 2, and 1 were assigned to normal conditions (4), and slightly (3), moderately (2) and severely (1) abnormal conditions, respectively. Cages were taken to a laminar flow hood and opened in order to clearly assess mouse activity. If a mouse showed significant signs of toxicity (e.g., ruffling, hunching, low activity, >15% weight loss), treatment was halted for that mouse until it fully recovered (i.e., weight returned to within 10% of starting weight).

Data analysis: For all study groups, maximum tumor growth inhibition was calculated for Day 11, 13, or 15 (Day X). This time point was the latest time point that had a sufficient number of tumors in all compared groups for statistical analysis. For each tumor, relative tumor size was calculated relative to its size on Day 1 when treatment was initiated (i.e., fold tumor growth). To calculate the maximum tumor growth inhibition for each tumor, the following equation was used: 100−(fold tumor growth drug-treated Day X/mean fold tumor growth vehicle-treated Day X)*100. Differences in tumor sizes between groups were determined using ANOVA analysis (GraphPad Prism 5 Software) where "*" refers to P=0.01-0.05 (significant), "" refers to P=0.001-0.01 (very significant) and "*" refers to P<0.001 (extremely significant), Differences that were not statistically significant are indicated with "ns". Tumor doubling times (dT) could not be calculated for this study because there was no tumor doubling during the treatment phase of the study for Groups 3 and 4. Tumor growth delay (T−C) was calculated by subtracting the median time for the control to reach the 1000 mm$^3$ size endpoint from that of the median time for the treated groups to reach the size endpoint. With respect to calculation of "time to reach [the tumor size] endpoint," it should be noted that some tumors in each group did not grow at all during the study.

Since these tumors were clearly not going to reach the endpoint, regardless of time, they were excluded from calculation of "time to reach endpoint" These tumors were not, however, excluded from any other analyses since they occurred with approximately equal frequency in all groups. TIC % was calculated as follows: (TdayX−Tday1)/(CdayX−Cday1)*100 where T and C represent the median tumor volume of treated tumors and C is the median tumor volume of control tumors on the designated days. This value represents the size of the treated tumor relative to the control tumor. Thus, a TIC %=40 means that the size of the treated tumor is 40% of the size of the control tumor at the designated time point. Differences in median survival time between study groups were analyzed using the LogRank test (GraphPad Prism 5 Software).

Figure 1B:
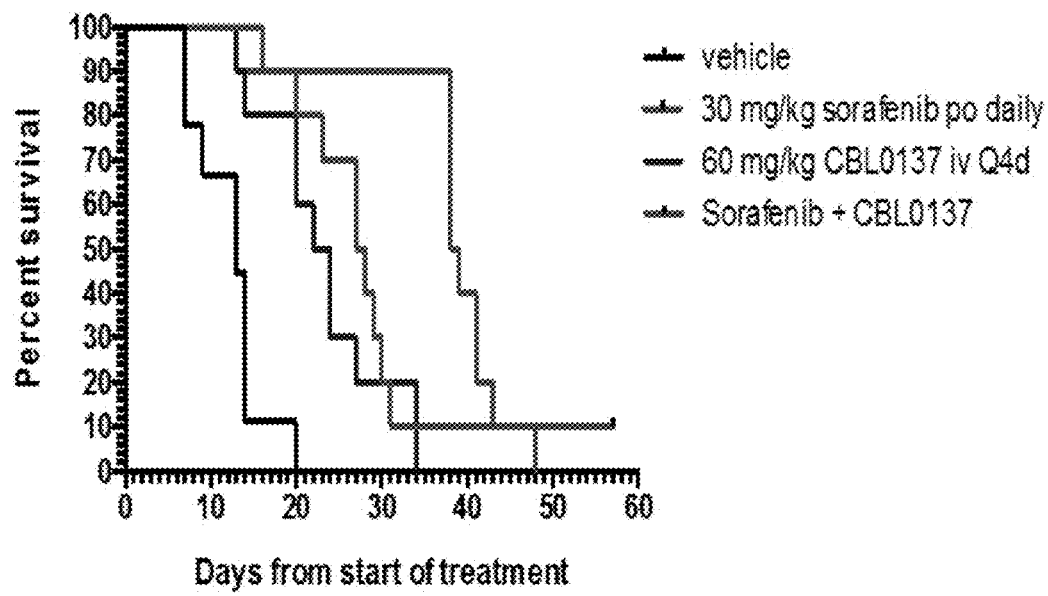
Figure 2A:
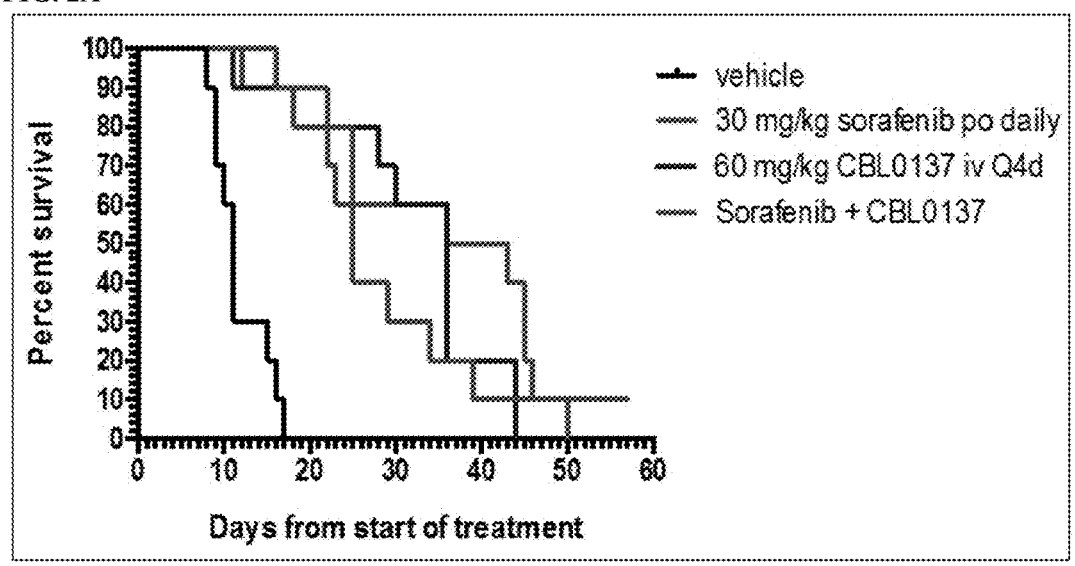
FIG. 2 shows Kaplan-Meier survival curves for groups of Hep3B tumor-bearing nude mice. Specifically, Panel A shows the survival curve of the (Hep3B study) tumor-bearing nude mice treated with (labeled from left to right) vehicle (first line) or different regimens of CBL0137 (second line), sorafenib (fourth line), or CBL0137+sorafenib (third line). Panel B shows the survival curve of the (Hep3B (sub-dose CBL0137) study) tumor-bearing nude mice treated with (labeled from left to right) vehicle (first line) or different regimens of CBL0137 (second line), sorafenib (third line), or CBL0137+sorafenib (fourth line).
Figure 2B:
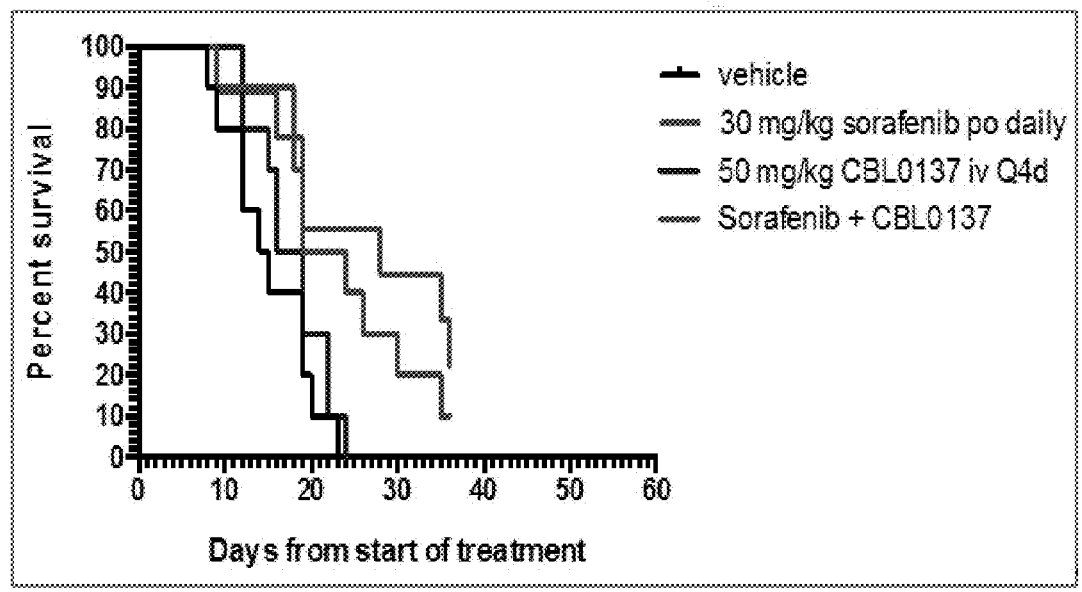

Example 1: Evaluation of CBL0137-Sorafenib Combination Treatment Against Hep2 G or Hep3B Hepatocellular Carcinoma Xenografts The kinetics of mortality for the HepG2 study is presented in FIG. 1, Panel A. There was no indication of any substantial impact of treatment toxicity on animal mortality in the study. Drug treatment did not cause on earlier onset of mortality or adversely affect (median survival times) MST relative to vehicle treatment. Differences in the kinetics of mortality and survival outcome in this study were primarily reflections of treatment efficacy, not toxicity. Likewise, the same results were observed for the HepG2 (sub-dose CBL0137) study, the Hep3B study, and the Hep3B (sub-dose CBL0137) study as presented in FIG. 1, Panel B; FIG. 2, Panel A; and FIG. 2, Panel B, respectively.

Analysis of the kinetics of survival of the HepG2 tumor-bearing mice (FIG. 1, Panel A) showed that the MST of 15 days observed in vehicle-treated Group 1 was not changed by treatment with sorafenib only (Group 2, MST=15 days) but was increased to 54.0 and 52.5 days, respectively, by treatment with CBL0137 only or CBL0137+sorafenib. These differences in MST reflected the effect of applied treatments on tumor growth, since mortality in this study, with the exception of one mouse, was due to tumor-related parameters not treatment toxicity (see above).

Analysis of the kinetics of survival of HepG2 (sub-dose CBL0137) tumor-bearing mice (FIG. 1, Panel B) showed that MST was increased from 13 days observed in vehicle-treated Group 1 to 27.5 days, 23 days, and 38.5 days in drug-treated Groups 2, 3, and 4, respectively. Moreover, the MST in combination-treated Group 4 was greater than that in either monotherapy group (P=0.0204 for combination versus sorafenib only and P=0.0001 for combination versus CBL0137 only). The difference between single drug-treated Groups 2 and 3 was not significant (P=0.373).

Analysis of the kinetics of survival of Hep3B tumor-bearing mice (FIG. 2, Panel A) showed that the median survival time (MST) of 11 days observed in vehicle-treated Group 1 was increased (P<0.0001) by all tested drug treatments. Accordingly, MST was increased to 25 days by sorafenib treatment, to 36 days by CBL0137 treatment, and to 39.5 days by CBL0137+sorafenib. While these MST values reflected the differences in other tumor growth parameters among the three different drug-treated groups, the differences in MST between drug-treated groups were not different. The duration of animal survival in this study was primarily a reflection of the kinetics of tumor growth to endpoint size rather than development of treatment toxicity.

The same trend of was observed by differences in the kinetics of survival of Hep3B (sub-dose CBL0137) tumor-bearing mice (FIG. 2, Panel B), The median survival time (MST) of vehicle-treated mice was 14.5 days as compared to 21.5, 17.5, and 28 days in sorafenib, CBL0137, and CBL0137+sorafenib-treated groups, respectively. Log Rank analysis in comparison to the vehicle-treated group showed that the observed increases in survival time were statistically significant for the CBL0137+sorafenib group (P=0.0092) as well as for the sorafenib monotherapy group (P=0.013), but not for the CBL0137 monotherapy group (P=0.2688). These differences in MST reflected the effect of drug treatment on tumor growth, since again, the mortality in this study was primarily due to tumor-related parameters not treatment toxicity.

Next, antitumor efficacy of the tested treatment regimens was established through measurement of tumors throughout the course of the study using digital calipers.

Figure 3B:
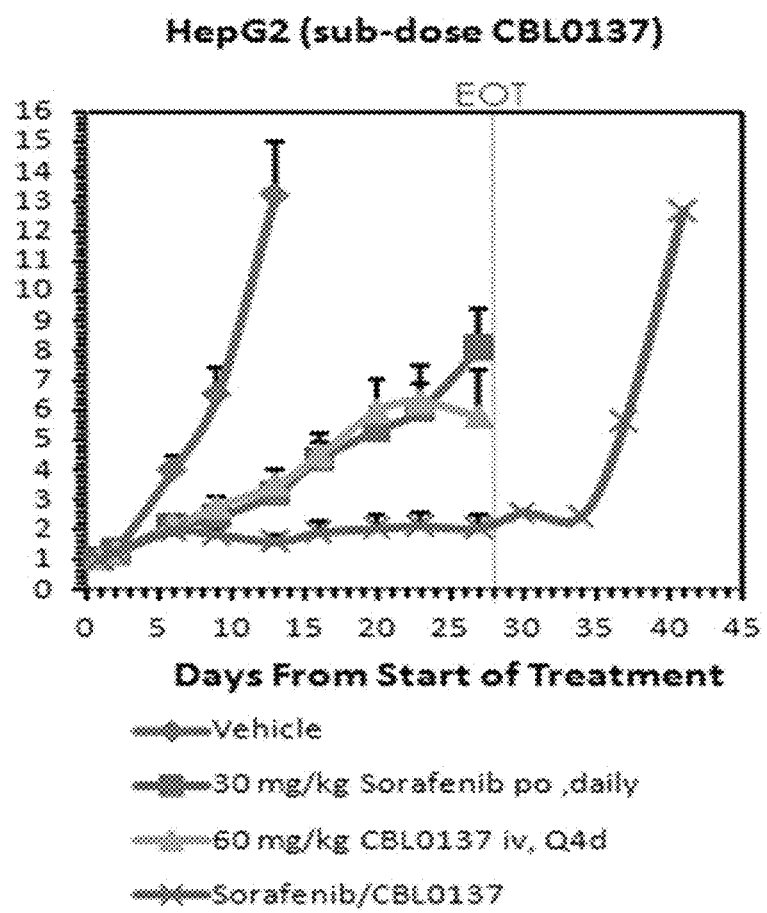
FIG. 3 shows mean fold-change in tumor volume in groups of HepG2 tumor-bearing nude mice. Panel A shows the mean fold-change in tumor volume (HepG2 study) of the tumor-bearing nude mice treated with vehicle or different regimens of CBL0137, sorafenib, or CBL0137+sorafenib. Panel B shows the mean fold-change in tumor volume (HepG2 (sub-dose CBL0137) study) of the tumor-bearing nude mice treated with vehicle or different regimens of CBL0137, sorafenib, or CBL0137+sorafenib. EOT represents end of treatment. Mean fold tumor growth was calculated by normalizing the tumor volume on Day X to that on Day 1 for each individual tumor (2 tumors per mouse) and then averaging the normalized values for all tumors in each group. For each group, data is presented for the time points at which there were a sufficient number of measurements to be representative of the group (i.e., measurements for ≥50% of the total number of animals in the group to prevent skewing of the data). Error bars represent the standard error of the means.

The kinetics of tumor growth in each study group (represented by the per-group mean fold-change in tumor volume on different days during the course of treatment relative to starting volume) is shown in FIG. 3 (Panels A and B) and FIG. 4 (Panels A and B), For the HepG2 study (FIG. 3, Panel A), Day 15 was selected for analysis of mean fold tumor growth because it was the latest time point at which there were sufficient data points in all groups for such analysis. On this day, the mean change in tumor volume versus Day 1 was 9.0-fold in Group 1 (vehicle), 8.4-fold in Group 2 (sorafenib only), 0.5-fold in Group 3 (CBL0137 only) and 0.9 in Group 4 (CBL0137+sorafenib). Mean fold tumor growth was lower in Group 3 and Group 4 than in either Group 1 or Group 2, but there was no difference between Groups 3 and 4 themselves. This mean fold tumor growth data indicated that tumors in Groups 3 and 4 did not grow, but rather regressed, during the first 15 days of the study. Consistent with this observation, T/C % values in both CBL0137 treatment groups (Groups 3 and 4) were negative (−3.5% and −3.3%, respectively) while the TIC % value of 72.6% in Group 2 illustrated the minimal effect of sorafenib monotherapy. In terms of individual tumors, 14 out of 16 tumors that grew in CBL0137-treated Group 3 and 13 out of 16 in CBL0137+sorafenib Group 4 demonstrated some degree of regression during the course of treatment. In contrast, 0/16 and 0/14 tumors that grew in vehicle-treated Group 1 and sorafenib-treated Group 2, respectively, showed similar behavior. The majority of regressing tumors did, however, begin to grow ~2 weeks after the end of the treatment phase of the study, and the overall (per-group mean) kinetics and extent of tumor growth during this period of growth was similar between Groups 3 and 4 (FIG. 3, Panel A).

In terms of the kinetics of tumor growth, tumor doubling time (dT) could not be calculated for the HepG2 study because there was no tumor doubling, but rather regression, during the treatment phase of the study for Groups 3 and 4. Tumor growth delay (T−C), based on the median time to reach the tumor size endpoint in treated (T) and control (C) groups, was 5.65 days with sorafenib treatment, as compared to 39.4 and 39.8 days with CBL0137 or CBL0137 sorafenib treatment, respectively. For these calculations, any tumors that did not grow at all during the course of the study (4/20, 6/20, 4/20 and 4/20 for Groups 1-4, respectively) were excluded since they would clearly not reach endpoint. It should be noted, however, that non-growing tumors were not excluded from any other analyses since they occurred with approximately equal frequency in all groups, One additional tumor in the vehicle-treated control Group 1 (Cage 2 Mouse 4) was excluded only from calculation of mean fold tumor growth on Day 15 (and the corresponding % growth inhibition on Day 15) because it did not appear to be a measurable size until after treatment commenced and therefore had no reference measurement to accurately assess the fold growth and level of inhibition.

For the HepG2 (sub-dose CBL0137) study, the kinetics of tumor growth in each study group is shown in FIG. 3, Panel B. Day 13 was selected for analysis of mean fold tumor growth because it was the latest time point at which there were sufficient data points in all groups for such analysis. On this day, the mean change in tumor volume versus Day 1 was 13.2-fold in Group 1 (vehicle), 3.2-fold in Group 2 (sorafenib only), 3.5-fold in Group 3 (CBL0137 only) and 1.6 in Group 4 (CBL0137 sorafenib). Thus, tumor growth between Days 1 and 13 was inhibited by 76% in Group 2, 74% in Group 3 and 88% in Group 4.

Mean fold tumor growth was lower in all three drug-treated groups (Groups 3, 4 and 5) than in vehicle-treated Group 1, Differences in mean fold-tumor growth between the drug-treated groups were not statistically significant on Day 13 because the tumors had just started to grow, At later time points (e.g., Day 23), differences in tumor growth were more apparent and there were sufficient surviving mice in Groups 2-4 for analysis. On Day 23, mean fold tumor growth was 6.02-fold and 6.26-fold in sorafenib-treated Group 2 and CBL0137-treated Group 3, respectively, as compared to 2.11-fold in combination-treated Group 4. The difference in mean fold tumor growth on Day 23 between the monotherapy groups was not significant (P=0.979), while that between the combination group and either monotherapy group was significant (P=0.0017 for comparison of combination versus sorafenib alone and P=0.0038 for comparison of combination versus CBL0137 alone).

Efficacy of CBL0137 and sorafenib (and to an even greater extent, CBL0137 sorafenib) in suppressing tumor growth was also illustrated by the T/C % values calculated for Day 13, These values indicated the tumors in Groups 2, 3 and 4 were 27.3%, 10.2% and 4.3% of the size of those in vehicle-treated Group 1, respectively.

In terms of the kinetics of tumor growth, tumor doubling time (dT) could not be calculated for the HepG2 (sub-dose CBL0137) study because tumors in the combination-treated Group 4 did not start to grow until after the treatment phase of the study was over. Tumor growth delay (T−C), based on the median time to reach the tumor size endpoint in treated (T) and control (C) groups, was 17 days with sorafenib treatment, 10 days with CBL0137 treatment and 29 days with CBL0137+sorafenib treatment. For these calculations, the median time to reach the tumor size endpoint in each group (12.6, 29.6, 22.5 and 41.6 days in Groups 1-4, respectively) was determined by extrapolation from exponential growth curves. The increase in median time to reach endpoint was statistically significant for all three drug-treated groups when compared to vehicle-treated Group 1. Among drug-treated groups, the median time to endpoint was greater in the sorafenib monotherapy group as compared to the CBL0137 monotherapy group (P=0.015); however, the median time to endpoint was even greater in the combination-treated group (P=0.001 for combination versus sorafenib alone and P<0.0001 for combination versus CBL0137 alone).

For the Hep3B study, the kinetics of tumor growth in each study group is shown in FIG. 4, Panel A. Day 11 was selected for analysis of mean fold tumor growth because it was the latest time point at which there were sufficient data points in all groups for such analysis. On this day, the mean change in tumor volume versus Day 1 was 9.08-fold in Group 1 (vehicle) as compared to 2.98-fold in Group 2 (sorafenib only), 1.05-fold in Group 3 (CBL0137 only) and 1.35 in Group 4 (CBL0137+sorafenib). Thus, tumor growth on Day 11 was inhibited by 67.2% in Group 2, 88.4% in Group 3 and 85.1% in Group 4. Mean fold tumor growth was lower in all three drug-treated groups (Groups 3, 4 and 5) than in vehicle-treated Group 1 (P<0.0001 for each pairwise comparison to Group 1). Differences in mean fold-tumor growth between the drug-treated groups were not statistically significant on Day 11 because the tumors had not grown substantially (in Group 2) or at all (in Groups 3 and 4) at that time point. At the latest time point with sufficient surviving mice in all three drug-treated groups for statistical analysis (i.e., Day 25), differences in tumor growth were more apparent: mean fold tumor growth was 8.22-fold in sorafenib-treated Group 2, 3.03-fold in CBL0137-treated Group 3 and 2.21-fold in combination-treated Group 4. Therefore, on average, tumors in the sorafenib monotherapy group had grown more by Day 25 than those in the CBL0137 monotherapy group (P=0.014) or in the combination group (P=0.008). In contrast, mean fold tumor growth on Day 25 was not different between the CBL0137 monotherapy group and the combination group (P=0.898)

Efficacy of sorafenib, and to an even greater extent, CBL0137 and CBL0137+sorafenib, in suppressing tumor growth was also illustrated by the TX % values calculated for Day 11. These values indicated the tumors in Groups 2, 3 and 4 were 33.4%, −6.4% and 2.5% of the size of those in vehicle-treated Group 1, respectively. The negative T/C % value calculated for CBL0137-treated Group 3 indicates that tumors actually shrank in size (regressed) in this group by Day 11.

In terms of the kinetics of tumor growth, tumor doubling time (dT), time to reach the tumor size endpoint, and tumor growth delay (T−C) could not be calculated for the Hep3B study because tumors in CBL0137-treated Group 3 and CBL0137+sorafenib-treated Group 4 did not grow substantially (and in many cases actually regressed, see below) during the treatment phase of the study.

Although the mean fold tumor growth values for both Days 11 and 25 indicated a small degree of tumor growth in CBL0137-treated Group 3 and combination-treated Group 4 (<3-fold), many of the individual tumors in these groups did not grow, but rather regressed (tumor volume was less than that at the start of treatment on Day 1), during the treatment phase of the study. Regression to 80% or less of starting volume was observed at some point during the treatment period for 11/20 tumors in Group 3 and for 8/19 tumors in Group 4. For all of these tumors, regression was not seen immediately upon the start of treatment, but developed after the tumors had grown slightly (e.g., after Day 8 or later). Growth of most of these tumors was only transiently suppressed; however, others never grew substantially (<2-fold growth versus Day 1) or continued to show regression (<1-fold growth versus Day 1) up until the animal was euthanized.

The kinetics of tumor growth for the Hep3B (sub-dose CBL0137) study in each study group is shown in FIG. 4, Panel B. It should be noted that the lack of efficacy observed in the study for CBL0137 monotherapy was, without wishing to be bound by theory, likely due to the suboptimal dose used (50 mg/kg as compared to its MTD of 70 mg/kg for every 4th day dosing). Multiple other studies in HCC and other tumor engraft models have demonstrated potent efficacy with 70 mg/kg CBL0137 administered iv Q4 d for 4 weeks (e.g. HepG2 study). In fact, in the Hep3B study, 60 mg/kg CBL0137 was very potent and required the reduction to 50 mg/kg for evaluating efficacy.

Day 15 was selected for analysis of mean fold tumor growth because it was the latest time point at which there were sufficient data points in all groups for such analysis. On this day, the mean change in tumor volume versus Day 1 was 21.0-fold in Group 1 (vehicle) as compared to 10.2-fold in Group 2 (sorafenib only), 13.0-fold in Group 3 (CBL0137 only) and 4.3-fold in Group 4 (CBL0137+sorafenib). Thus, tumor growth between Days 1 and 15 was inhibited by 51.4% in Group 2, 38.2% in Group 3 and 79.6% in Group 4. The reduction in mean fold tumor growth on Day 15 in the combination-treated group (Group 4) was statistically significant compared to vehicle-treated Group 1 ($P<0.0053$; Table 3.2.1). However, the differences in mean fold tumor growth between either monotherapy group (Group 2 or 3) and the vehicle group were not significant ($P>0.05$).

Analysis of all other parameters of tumor growth (dT, time to endpoint, growth delay, T/C %) gave similar results: a trend towards increased antitumor efficacy in drug-treated groups was observed with CBL0137 monotherapy having a noticeable beneficial effect over vehicle treatment, sorafenib monotherapy having a stronger beneficial effect, and the CBL0137+sorafenib combination have the strongest effect. For parameters amenable to statistical analysis (dT and median time to endpoint), the differences between the combination- and vehicle-treated groups were highly statistically significant ($P<0.0001$), while those between either single-drug group and the vehicle group did not reach statistical significance ($P>0.05$; although the difference in median time to endpoint between the sorafenib-treated and vehicle-treated groups was near-significant: $P=0.0534$).

Consistent with the finding that CBL0137 sorafenib treatment was efficacious against Hep3B tumors as compared to vehicle, while the single drugs were not, direct comparison of the three drug-treated groups showed that, in general (for most parameters), the combination was more effective than either single drug and there was no statistical difference between the single drug groups. This was the case for dT, time to endpoint, and % growth inhibition on Day 15 (for comparison of combination to CBL0137 only). Mean fold tumor growth on Day 15 was highest in Group 3 (06L0137 only; 13.0-fold), followed by Group 2 (sorafenib only; 10.2-fold) and then Group 4 (CBL0137+sorafenib; 4.3-fold), but these differences did not reach statistical significance. Later in the Hep3B (sub-dose CBL0137) study, differences in mean tumor growth between drug-treated groups were more apparent, as the tumors in the single-drug treatment groups continued to grow exponentially while those in the combination treatment group were suppressed. Thus, on Day 19 (the latest time point with sufficient surviving mice in all three drug-treated groups for statistical analysis), mean fold tumor growth was 19.5-fold and 21.8-fold in Groups 2 and 3, respectively, as compared to 5.6-fold in Group 4. At this time point, the reduction in mean fold tumor growth in the combination-treated group compared to either monotherapy group was close to statistically significant ($P=0.0666$ for comparison of Groups 2 and 4, and $P=0.0522$ for comparison of Groups 3 and 4). MST was increased in both the CBL0137+sorafenib group ($P=0.0216$) and the sorafenib monotherapy group ($P=0.0415$) relative to the CBL0137 monotherapy group, but the difference between CBL0137+sorafenib group and sorafenib was not significant ($P=0.3819$).

In summary, without wishing to be bound by theory, the HepG2 results showed that while treatment with sorafenib alone had no effect against HepG2 tumor growth, treatment with CBL0137 was highly efficacious. Addition of sorafenib to the CBL0137 regimen did not enhance its antitumor effects under the conditions used in the study. For the HepG2 (sub-dose CBL0137) study, without wishing to be bound by theory, the results showed that the tested regimens of sorafenib monotherapy and CBL0137 monotherapy effectively suppressed HepG2 tumor growth and displayed similar levels of efficacy. Surprisingly, combination of the sorafenib and CBL0137 regimens resulted in greater antitumor efficacy than treatment with either drug alone (synergy).

Additionally, without wishing to be bound by theory, the Hep3B results showed that the applied regimens of sorafenib monotherapy, CBL0137 monotherapy, and CBL0137+sorafenib combination treatment were all efficacious in suppressing growth of Hep3B engrafts. However, CBL0137 and CBL0137+sorafenib were more effective as antitumor agents in this model than sorafenib. The level of tumor suppression provided by CBL0137 and CBL0137+sorafenib was similar, most likely due to the combined effects of (i) strong efficacy of the applied dose of CBL0137, and (ii) reduced dosing with sorafenib in the combination-treated group due to animal weight loss. Therefore, it was not possible in the Hep3B study to determine whether combination of the two drugs lead to enhanced antitumor efficacy. This situation is similar to that observed in the HepG2 study, where the applied dose of CBL0137 was highly efficacious against HepG2 HCC engrafts and thus, prevented observation of any additional benefit upon combination of CBL0137 and sorafenib. The subsequent study in the HepG2 model performed with adjusted drug doses (HepG2 (sub-dose CBL0137) study) revealed enhanced efficacy of CBL0137+sorafenib combination compared to that of either drug alone. Similar results, without wishing to be bound by theory, were observed in the Hep3B model performed with adjusted drug doses (Hep3B (sub-dose CBL0137) study).

Figure 5A:
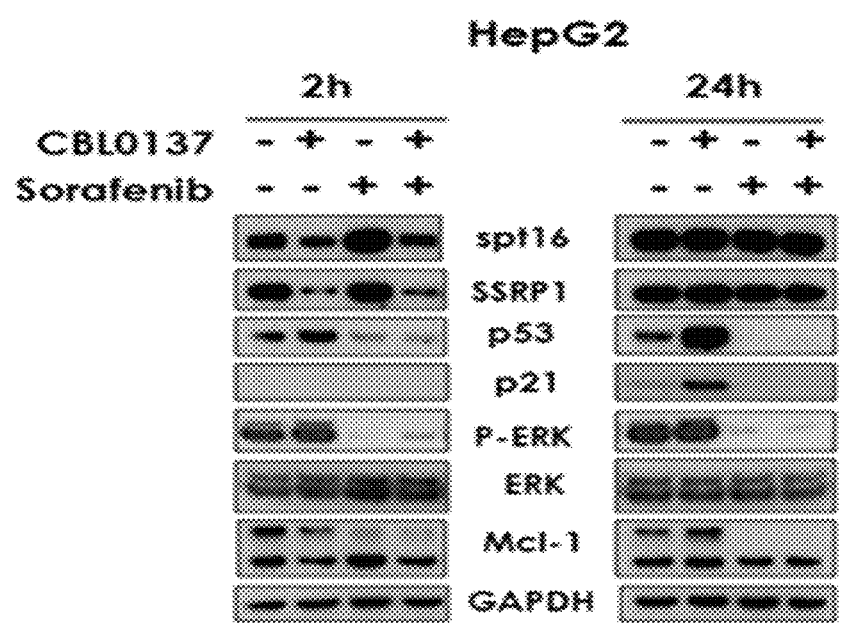
FIG. 5 shows Western blot analysis for the HepG2 or Hep3B tumor-bearing nude mice treated with vehicle, CBL0137, sorafenib, or CBL0137+sorafenib after 2 and 24 h. Specifically, the Western blots monitored expression of spt16, SSRP1, p53, p21, P-ERK, ERK, Mcl-1, and GAPDH (control). Panel A corresponds to the tumor-bearing nude mice from the HepG2 study whereas Panel B corresponds to the tumor-bearing nude mice from the Hep3B study.
Figure 5B:
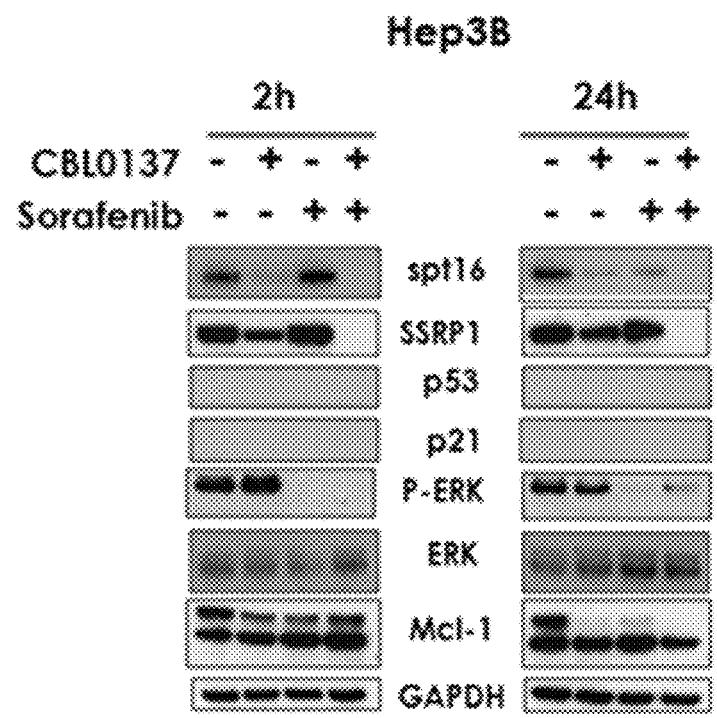

Similar mouse studies as above were conducted in vitro to determine the possible mechanism of CBL0137+Sorafenib combination treatment on tumor suppression. FIG. 5 (Panels A and B) shows results from Western blots run from the HepG2 and Hep3B tumor-bearing mice after 2 and 24 h post vehicle, CBL0137, sorafenib, or CBL0137+sorafenib treatment. Specifically, the Western blots monitored the effect of drug treatment on expression of spt16, SSRP1, p53, p21, P-ERK, ERK, Mcl-1, and GAPDH (control) proteins, of which most are involved in cell cycle progression and regulation. SSRP1/spt16 is a known target for CBL0137 activity, hence, CBL0137 caused subunits to become tightly bound (reversibly) leading to a decrease in expression at 2 h. CBL0137 is known to induce p53 and the p53 target, p21 (HepG2 only since Hep3B is p53 null) but as seen in the Western blot, sorafenib blocked this induction. Sorafenib is known to block phosphorylation of P-ERK as well as cause down regulation of Mcl-1. CBL0137 did not affect this in the combination treatment.

Additional in vitro studies were conducted in order to elucidate a possible mechanism of the CBL0137+sorafenib combination treatment on tumor suppression. FIG. 6 (Panels A-D) shows the effect of CBL0137, sorafenib, or CBL0137+sorafenib treatment on the expression of NF-κB target genes (IL-8 and TNF) for the tumor-bearing nude mice (HepG2 and Hep3B) measured using real-time PCR with gene specific primers and probe. CBL0137 is known to inhibit NF-κB. Thus, at 2 h after exposure to the drug, expression of the NF-κB target genes (IL-8 and TNF) should decrease. This was observed for both basal NF-κB mediated transcription and TNF-induced NF-κB activity. Sorafenib was also observed to have an effect on expression of NF-κB target genes, albeit less than CBL0137. Finally, strong synergy was observed between CBL0137 and sorafenib with respect to the expression of the NF-κB genes, with almost complete abrogation of expression of both TNF and IL-8 in both HCC cell lines. Without wishing to be bound by theory, the combined effect of CBL0137 and sorafenib appeared to be, in part, due to effects on the NF-κB pathway.

Example 2: Evaluation of CBL0137-Gemcitabine Combination Treatment Against Pancreatic Cancer (or 111975 Non-Small Cell Lung Cancer Xenografts)

Similar mouse studies as described in Example 1 were performed to determine the effect of CBL0137+gemcitabine combination treatment against pancreatic and non-small cell lung cancer. The kinetics of mortality for the PDA different study groups is presented in FIG. 7, Panel A. There was no indication of any substantial impact of treatment toxicity on animal mortality in this study. Drug treatment did not cause an earlier onset of mortality or adversely affect MST relative to vehicle treatment. No mice in the study were euthanized due to excessive weight loss/morbidity. All mortality in the study was due to tumors reaching the size endpoint or, in the case of one combination-treated animal, reaching the end of the study (Day 89). Therefore, differences in the kinetics of mortality and survival outcome in this study were primarily reflections of treatment efficacy, not toxicity, and are further discussed below.

Figure 7A:
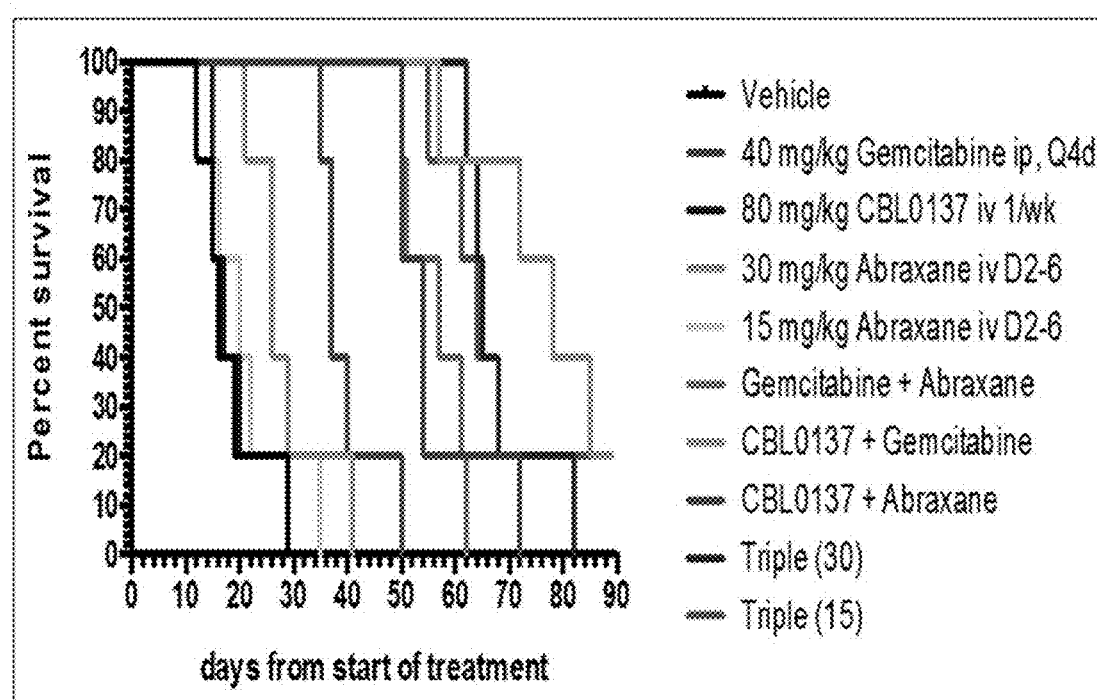
FIG. 7 shows Kaplan-Meier survival curves for groups of PDA tumor-bearing SCID mice. Specifically, Panel A shows the survival curve of the (PDA #13756 study) tumor-bearing SCID mice treated with (labeled from left to right) vehicle (first line) or different regimens of CBL0137 (second line), gemcitabine (seventh line), or CBL0137+gemcitabine (tenth line). Panel B shows the survival curve of tumor-bearing SCID mice treated with (labeled from left to right) vehicle (first line) or different regimens of CBL0137 (second line), gemcitabine (fourth line), or CBL0137+gemcitabine (ninth line).
Figure 7B:
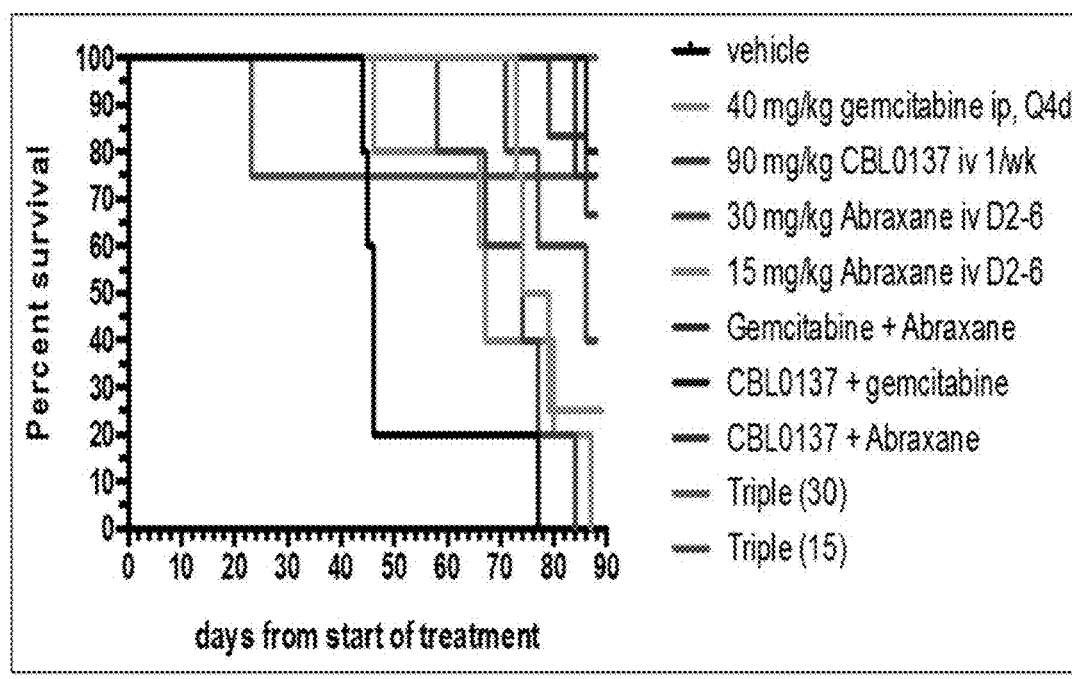

The kinetics of mortality for the PDA different study groups is presented in FIG. 7, Panel B. MST could not be accurately calculated for the double-drug combination groups due to survival of the majority of the mice in these groups to the end of the study (day 88). Mortality in this study was primarily due to tumor growth, not treatment toxicity. Also, differences in the kinetics of mortality and survival outcome in the study were primarily reflections of treatment efficacy, not toxicity, and are further discussed below.

Figure 8A:
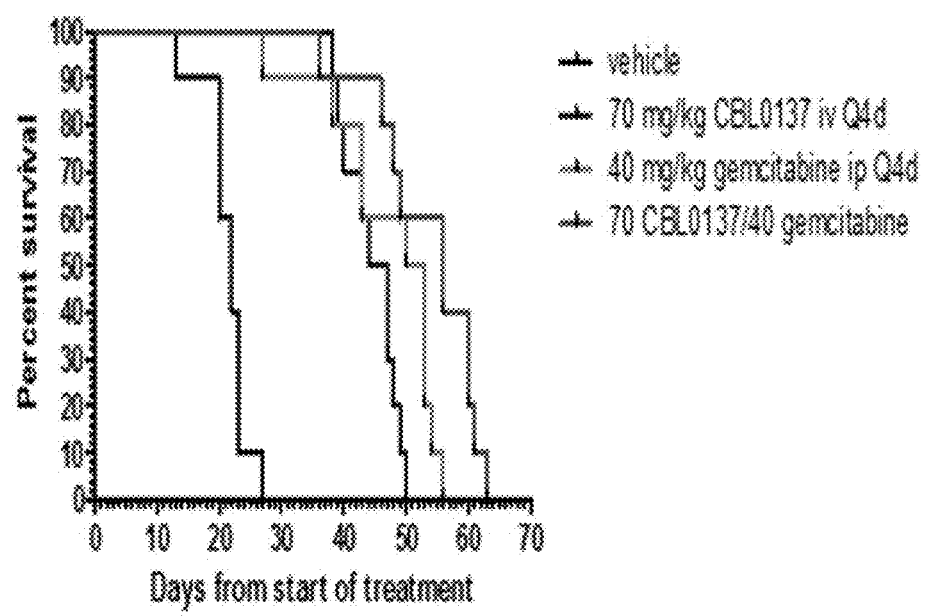
FIG. 8 shows Kaplan-Meier survival curves for groups of H1975 NSCLC tumor-bearing nude mice. Specifically, Panel A shows the survival curve of the (H1975 NSCLC Study 1) tumor-bearing nude mice treated with (labeled from left to right) vehicle (first line) or different regimens of CBL0137 (second line), gemcitabine (third line), or CBL0137+gemcitabine (fourth line). Panel B shows the survival curve of the (H1975 NSCLC Study 2) tumor-bearing nude mice treated with (labeled from left to right) vehicle (third line) or different regimens of CBL0137 (sixth line), gemcitabine (fourth line), or CBL0137+gemcitabine (fifth line).

The kinetics of mortality for the NSCLC Study 1 different study groups is presented in FIG. 8, Panel A. None of the cage-side observations were indicative of any toxicity of the tested regimens (CBL0137 monotherapy, gemcitabine monotherapy or CBL0137+gemcitabine combination) during the course of the study. All mortality in the study resulted from euthanasia triggered by tumors reaching the 2000 mm$^3$ size endpoint. Therefore, median survival time was directly related to tumor burden and is discussed below.

The kinetics of mortality for the NSCLC Study 2 different study groups is presented in FIG. 8, Panel B. In the four study groups (vehicle, CBL0137, gemcitabine, and CBL0137+gemcitabine), there were no signs of morbidity in any of the animals. Drug treatment in these groups did not cause an earlier onset of mortality or adversely affect MST relative to vehicle treatment. All mortality in Groups 1, and single drug treatment resulted from euthanasia due to tumors reaching the 2000 mm$^3$ size endpoint. For two mice in CBL0137+gemcitabine, the tumors were noted to be ulcerated at the time of euthanasia, but also approaching the size endpoint (1547 and 1921 mm$^3$). Two mice in the study (both from CBL0137-treated group) survived to Day 89 (the end of the study). One of these mice was excluded from all analyses because its "tumor" was actually found to be an enlarged lymph node upon necropsy rather than a tumor. The other mouse that survived to Day 89 had a tumor that was approaching endpoint size (1643 mm$^3$). Therefore, MST was directly related to tumor burden and is discussed below.

Next, antitumor efficacy of the tested treatment regimens was established through measurement of tumors throughout the course of the study using digital calipers.

Figure 9A:
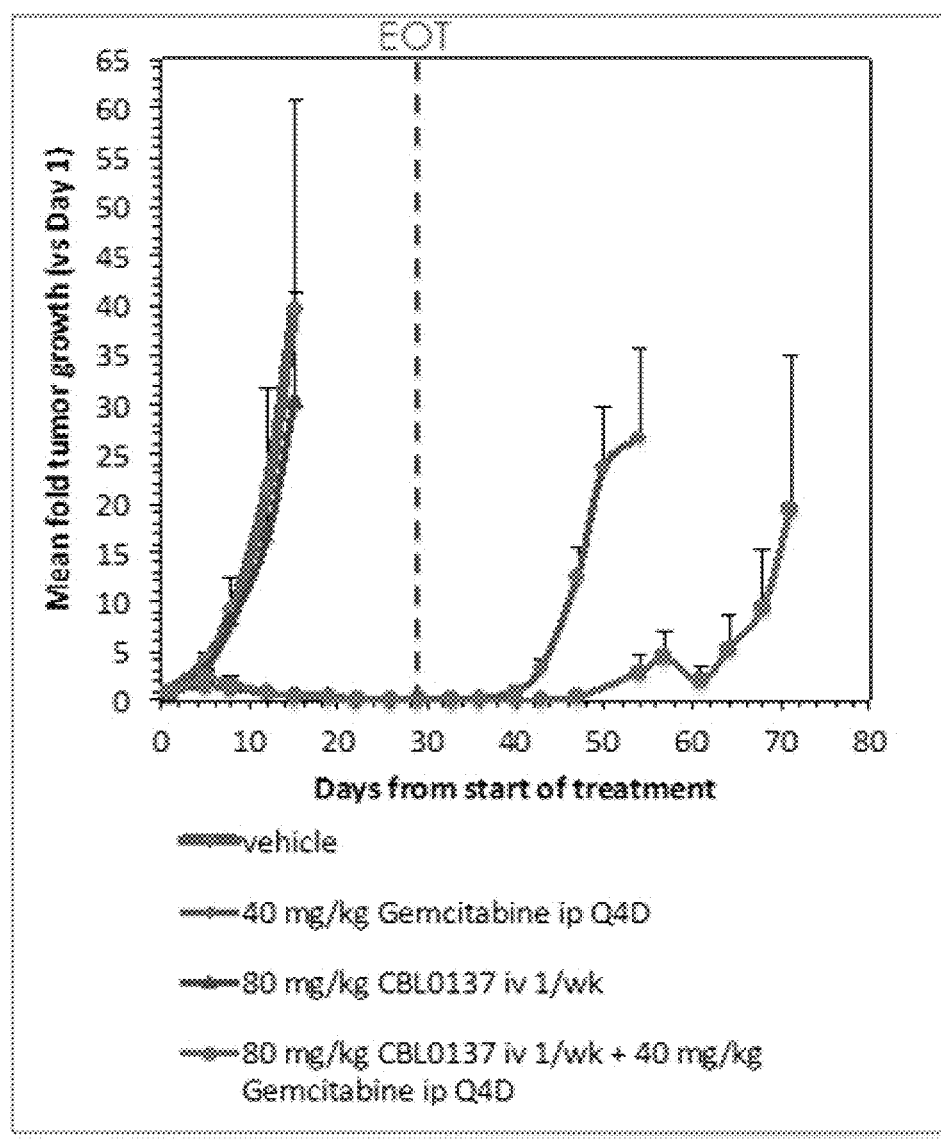
FIG. 9 shows mean fold-change in tumor volume in groups of PDA tumor-bearing SCID mice. Specifically, Panel A shows the mean fold-change in tumor volume of the tumor-bearing SCID mice treated with (labeled from left to right) vehicle (first line) or different regimens of CBL0137 (second line), gemcitabine (third line), or CBL0137+gemcitabine (fourth line). Panel B shows the mean fold-change in tumor volume (PDA #13590 study) of the tumor-bearing SCID mice treated with (labeled from left to right) vehicle (first line) or different regimens of CBL0137 (second line), gemcitabine (third line), or CBL0137+gemcitabine (fourth line). LOT represents end of treatment. Mean fold tumor growth was calculated by normalizing the tumor volume on Day X to that on Day 1 for each individual tumor (2 tumors per mouse) and then averaging the normalized values for all tumors in each group. For each group, data is presented for the time points at which there were a sufficient number of measurements to be representative of the group (i.e., measurements for ≥50% of the total number of animals in the group to prevent skewing of the data). Error bars represent the standard error of the means.
Figure 10A:
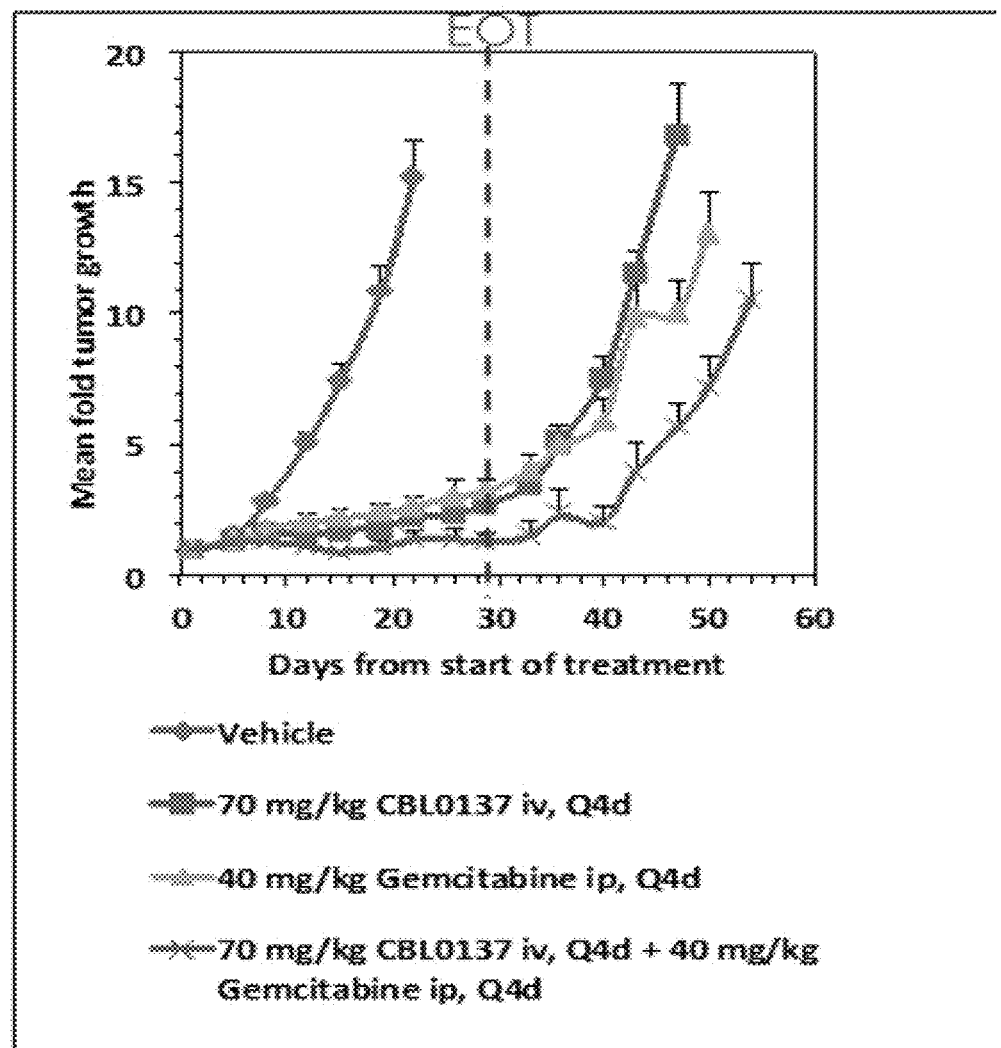
FIG. 10 shows mean fold-change in tumor volume in groups of H1975 NSCLC tumor-bearing nude mice. Specifically, Panel A shows the mean fold-change in tumor volume of the tumor-bearing nude mice treated with vehicle or different regimens of CBL0137, gemcitabine, or CBL0137+gemcitabine. Panel B shows mean fold-change in tumor volume (H1975 NSCLC Study 2) of the tumor-bearing nude mice treated with vehicle or different regimens of CBL0137, gemcitabine, or CBL0137 gemcitabine. LOT represents end of treatment. Mean fold tumor growth was calculated by normalizing the tumor volume on Day X to that on Day 1 for each individual tumor (2 tumors per mouse) and then averaging the normalized values for all tumors in each group. For each group, data is presented for the time points at which there were a sufficient number of measurements to be representative of the group (i.e., measurements for ≥50% of the total number of animals in the group to prevent skewing of the data). Error bars represent the standard error of the means.
Figure 10B:
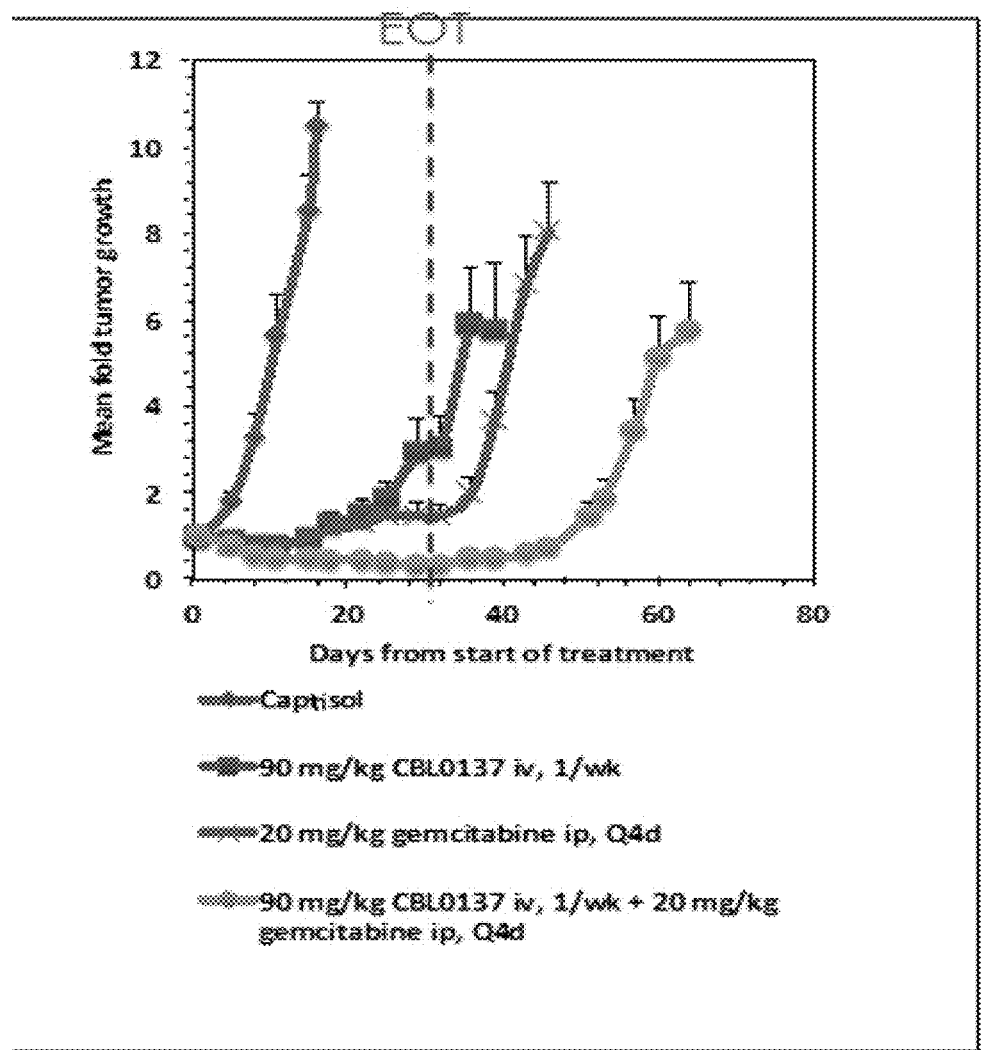
Figure 12A:
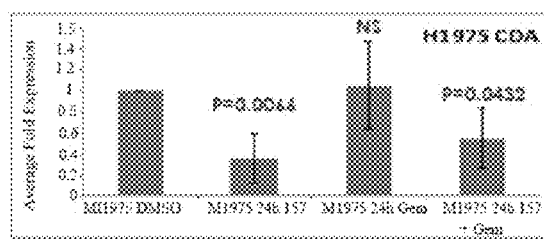
FIG. 12 shows the effect of CBL0137±gemcitabine (or DMSO as a control) on CDA and dCK expression in PDA and NSCLC (H1975 and A549) cell lines in vitro. Specifically, Panel A corresponds to H1975 CDA, Panel B corresponds to H1975 dCK, Panel C corresponds to A549 CDA, Panel D corresponds to A549 dCK, Panel E corresponds to MiaPaca2 CDA, and Panel F corresponds to MiaPaca2 dCK.
Figure 12B:
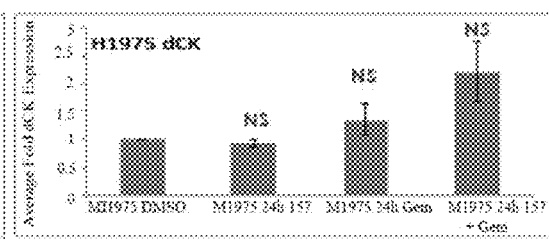
Figure 12C:
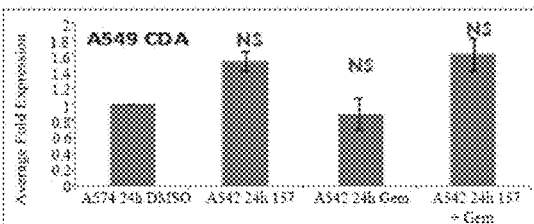
Figure 12D:
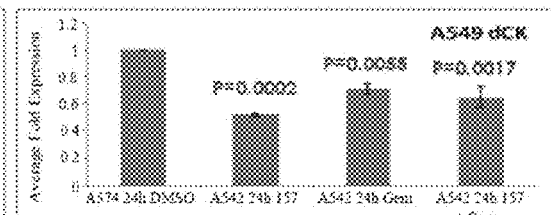
Figure 12E:
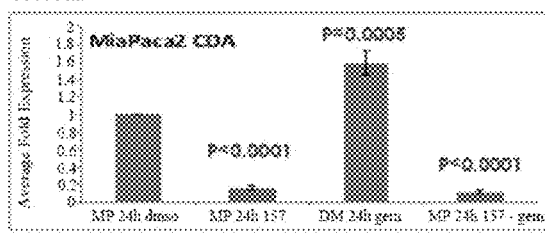
Figure 12F:
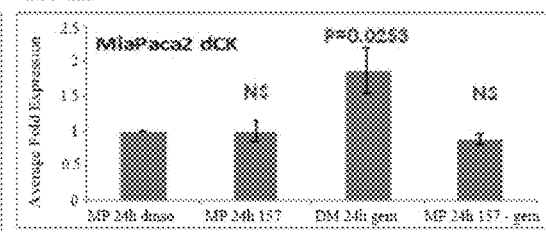

The kinetics of tumor growth for each FDA and NSCLC study (represented by the per-group mean fold-change in tumor volume on different days during the course of treatment relative to starting volume) is shown in FIGS. 9 and 10 (Panels A and B).

Specifically, FIG. 9, Panel A shows the kinetics of tumor growth in each study group for the FDA #13756 study. In order to compare all drug-treated groups to the vehicle-treated group, tumor growth was assessed at Day 15, the latest time point at which there were sufficient data points in all groups for analysis. All tested drug treatments except for CBL0137 monotherapy demonstrated antitumor efficacy in comparison to vehicle-treated Group 1. This efficacy was revealed in reduction in mean fold tumor growth on Day 15 compared to vehicle control, as well as reduced size of treated tumors relative to control tumors on Day 15 (T/C %) and increased time for tumors to reach the size endpoint. For gemcitabine alone and CBL0137+gemcitabine, mean fold tumor growth on Day 15 was <1.0, indicating that tumors not only failed to grow, but actually shrank relative to their size at the start of drug treatment. Indeed, the majority of individual tumors in these groups (8/10 and 5/6, respectively) had regressed or disappeared (no measurable tumor)

by Day 15, It should be noted that the lack of efficacy of CBL0137 monotherapy in this study was likely due to the selected dose. The maximum tolerated dose and optimal dose of CBL0137 for 1×/week dosing regimens for antitumor efficacy studies is 90 mg/kg CBL0137.

In order to assess potential additive/synergistic effects of different drug combinations, which were generally not discernable early in the treatment period (i.e., Day 15, the last time point at which comparisons with the vehicle control group could be made), tumor growth was also evaluated on Day 29 (the last day of the treatment period) and on Day 54 (the latest time point with sufficient mice remaining in compared groups for analysis), where possible. Comparison of gemcitabine, CBL0137 and their combination showed that, at Day 15, tumor growth in both the gemcitabine and gemcitabine+CBL0137 groups was reduced in comparison to the CBL0137 group. Thus, compared to the 30.4-fold mean tumor growth on Day 15 in the CBL0137 group, tumors grew 0.55-fold in the gemcitabine group (P=0.0014) and 0.4-fold in the gemcitabine+CBL0137 group (P=0.0075). The effect of gemcitabine and gemcitabine+CBL0137 on tumor growth at Day 15 was not different (P>0.999). At Day 29, there were not sufficient tumors for analysis of the CBL0137 group, but the gemcitabine and gemcitabine+CBL0137 groups remained indistinguishable in terms of tumor growth (regression of all tumors in both groups). By Day 54, tumors had begun to grow in both groups; however, those in the gemcitabine+CBL0137 group grew slower than those in the gemcitabine monotherapy group. Thus, on Day 54, mean fold tumor growth in the gemcitabine group was 26.7-fold, while that in the gemcitabine+CBL0137 group was only 2.8-fold (P=0.009). The greater efficacy of gemcitabine+CBL0137 over either single drug was also indicated by the prolonged animal survival time in the combination-treated group (78 days versus 54 days with gemcitabine alone (P=0.0153) and versus 17 days with CBL0137 alone (P=0.0017). These results indicated, without wishing to be bound by theory, that CBL0137 enhanced the effects of gemcitabine even under conditions in which it was not effective on its own.

FIG. 9, Panel B shows the kinetics of tumor growth in each study group for the PDA study. In order to compare all drug-treated groups to the vehicle-treated group, tumor growth was assessed at Day 29, the last day of the treatment period. All tested drug treatments demonstrated antitumor efficacy in comparison to vehicle-treated Group 1. This efficacy was revealed by reduction in mean fold tumor growth on Day 29 compared to the vehicle-treated control group. These reductions in mean fold tumor growth corresponded to 66.9% to 98.1% tumor growth inhibition. The tumor suppressive effect of all tested drug treatments was also illustrated by the smaller size of treated tumors relative to control tumors on Day 29 (T/C %) and increased time for tumors to reach the size endpoint. For all drug-treated groups except for CBL0137 alone, mean fold tumor growth on Day 29 was <1.0, indicating that on average, tumors not only failed to grow, but actually shrank relative to their size at the start of drug treatment. Only 1/9 and 3/10 individual tumors showed regression at Day 29 in the vehicle and CBL0137 groups, respectively. In contrast, the majority of individual tumors in the groups treated with gemcitabine (6/6), and CBL0137+gemcitabine (8/8) regressed or disappeared (no measurable tumor) by Day 29. The ability of each tested single-drug regimen to suppress tumor growth was also indicated by prolonged survival in those groups as compared to the vehicle group. Thus, MST was increased from 46 days in the vehicle group to 76.5 and 74 days in groups treated with gemcitabine and CBL0137, respectively. MST could not be evaluated for the double-drug treated group since the majority of animals in this group survived to the end of the study. However, even without calculation of MST per se, the potent efficacy of the combination treatment is supported by the finding that no (0/5) vehicle-treated animals survived to the end of the study, while 3/5 animals in gemcitabine+CBL0137 did.

For comparison of the relative antitumor efficacy of different drug treatments, tumor growth was assessed not only at Day 29 (the last time point at which comparisons with the vehicle control group could be made), but also on Day 57 (one month after the end of the treatment period) and on Day 71 (the latest time point with sufficient mice remaining in compared groups for analysis), when tumors had started growing more in all groups and differences between groups were more apparent. These analyses (mean fold tumor growth on Day 29 and mean fold tumor growth on Days 57 and 71) as well as analysis of animal survival time (MST) showed that there were no differences in the antitumor effects of the tested single-drug treatments gemcitabine and CBL0137.

Comparison of gemcitabine, CBL0137, and their combination showed that at all three analyzed time points (Days 29, 57 and 71), mean fold tumor growth was lower in the combination group, then in the gemcitabine group and the CBL0137 group. For example, at the latter time points where differences between groups were most apparent, mean fold tumor growth values on Day 57 were 0.75±0.13 with combination treatment, 7.91±2.7 with gemcitabine treatment, and 10.95±3.1 with CBL0137 treatment; corresponding mean fold tumor growth values on Day 71 were 2.22±0.94, 12.98±3.9, and 16.13±5.7. As mentioned above, the differences in mean fold tumor growth between gemcitabine and CBL0137 monotherapies were not substantial at any time point. Differences in tumor growth between the gemcitabine group and the combination group were substantial (5-10-fold) at both Day 57 and Day 71 (the difference at Day 71 was P=0.072). Because of the slightly lower efficacy of CBL0137 monotherapy compared to gemcitabine monotherapy, the differences in tumor growth between the CBL0137 group and the combination group were P=0.0085 for fold tumor growth on D57 and P=0.0065 for fold tumor growth on D71. Enhanced efficacy of the gemcitabine+CBL0137 combination over either drug alone was also indicated by differences in animal survival. Although MST could not be calculated and evaluated for the combination-treated group (since the majority of animals survived to the end of the study), survival was prolonged in the combination group (⅘ animals surviving to the end of the study on Day 88; MST >88 days) as compared to both the gemcitabine group (¼ animals surviving to Day 88; MST=76.5 days) and the CBL0137 group (0/5 animals surviving to Day 88; MST=74 days). These results indicated, without wishing to be bound by theory, that while both CBL0137 and gemcitabine were effective against PDA #13590 tumor growth as single agents, their combination resulted in enhanced efficacy. While the beneficial effect of combining the drugs was only statistically significant in comparison to CBL0137 monotherapy, the effect was also substantial in comparison to gemcitabine monotherapy. Without wishing to be bound by theory, these results indicated that while both CBL0137 and gemcitabine were effective against PDA #13590 tumor growth as single agents, their combination resulted in enhanced efficacy.

FIG. 10, Panel A shows the kinetics of tumor growth in each study group for the H1975 NSCLC Study 1. Day 22 was selected for analysis of mean fold tumor growth because it was the latest time point at which there were sufficient data points in all treatment groups. This analysis showed that all tested regimens of treatment provided antitumor efficacy as compared to vehicle treatment. Mean fold tumor growth on Day 22 was reduced from 15.2 in the vehicle-treated Group 1 to 2.2, 2.7, and 1.4, in drug-treated groups of CBL0137 alone, gemcitabine alone, or a combination of the two, respectively. The most effective regimens were CBL0137+ gemcitabine combination, then CBL0137 monotherapy, and then gemcitabine monotherapy, which corresponded to tumor growth inhibition on Day 22 of 90.8%, 85.3% and 82.6%, respectively. The kinetics of tumor growth shown in FIG. 10, Panel A also indicated greater separation at later time points. Analyses were repeated for mean fold tumor growth at Day 29 (the end of the treatment period) and Day 40, where tumors of single drug-treated animals, but not combination-treated animals, were growing exponentially. These analyses indicated that at both of these later time points, the high dose combination of CBL0137+gemcitabine was more effective at suppressing H1975 tumor growth than either drug administered as a monotherapy.

The antitumor efficacy of all regimens was confirmed by other parameters of tumor growth evaluated, including time to reach endpoint, growth delay, T/C %, and median survival time (MST). For example, MST was increased from 22 days in the vehicle control Group 1 to 45.5, 51.5, 56 days in the drug treated groups of CBL0137, gemcitabine, or a combination of the two, respectively. As discussed above, survival curves illustrating the kinetics of mouse survival in the study are shown in FIG. 8, Panel A.

FIG. 10, Panel B shows the kinetics of tumor growth in each study group for the H1975 NSCLC Study 2. For evaluation of the antitumor efficacy of all tested treatments, Day 5 was selected for analysis of mean fold tumor growth because it was the latest time point at which there were sufficient data points in all treatment groups. The analysis showed that all tested regimens of treatment provided significant antitumor efficacy as compared to vehicle treatment. Mean fold tumor growth on Day 5 was reduced from 1.76-fold in vehicle-treated Group 1 to <1.0-fold in all other study groups (P<0.0001). Mean fold tumor growth <1.0 was indicative of tumor regression and, indeed, 6/9, 9/10, and 9/10 individual tumors in CLB0137, gemcitabine, and a combination of the two, respectively were smaller on Day 5 than they were at the start of treatment on Day 1 (as compared to 1/9 in Group 1), The antitumor efficacy of CBL0137, gemcitabine and CBL0137+gemcitabine treatments was also reflected by increases in MST. While MST was 16 days in vehicle-treated Group 1, it was prolonged to 40, 48.5 and 66 days in CBL0137, gemcitabine, and CBL0137+gemcitabine, respectively (P<0.0001 for comparison of each drug-treated group to the vehicle group).

Efficacy of CBL0137, gemcitabine and CBL0137+gemcitabine was further analyzed at both Day 15 (the last day on which there were sufficient animals in the groups for comparison of drug-treated groups to the vehicle group) and at Day 39 (the last day on which there were sufficient animals in the group for comparison between drug-treated groups). In comparing the CBL0137, gemcitabine and CBL0137+ gemcitabine groups to the vehicle group, as seen on Day 5, mean fold tumor growth on Day 15 was reduced by all three regimens of drug treatment. Thus, mean fold tumor growth was 0.92-, 0.958- and 0.461-fold in CBL0137, gemcitabine, and CBL0137+gemcitabine, respectively, versus 8.52-fold in vehicle-treated Group 1 (P<0.0001 for comparison of each drug-treated group to the vehicle group). This corresponded to 89.2%, 88.8% and 94.6% tumor growth inhibition on Day 15 in CBL0137, gemcitabine, or a combination of the two, respectively. The potent antitumor efficacy of the CBL0137, gemcitabine and CBL0137+gemcitabine regimens was confirmed by additional parameters of tumor growth, including time to reach endpoint and growth delay, and T/C %. The median time to reach endpoint was increased from 15.6 days with vehicle treatment to 39.5, 47.8 and 66.2 days with CBL0137, gemcitabine and CBL0137+gemcitabine treatment, respectively (P<0.0001 for comparison of each drug-treated group to the vehicle group). This corresponded to a delay in tumor growth (relative to vehicle treatment) of 23.9 days with CBL0137, 32.2 days with gemcitabine, and 50.5 days with CBL0137+ gemcitabine. As mentioned above, increased MST (relative to vehicle treatment) was an additional indication of the antitumor efficacy of CBL0137, gemcitabine and CBL0137+gemcitabine in the study.

CBL0137, gemcitabine, or a combination of the two was further analyzed in order to determine whether combination of CBL0137 and gemcitabine resulted in enhanced efficacy as compared to treatment with either single drug. Later in the study, particularly after the treatment period ended on Day 29, tumors in both single drug treated groups began to grow at a much faster rate, while those in the CBL0137+gemcitabine group continued to be suppressed. Therefore, on Day 39 (the last day of the study with sufficient surviving animals in the groups for comparison), mean fold tumor growth was lower in the CBL0137+gemcitabine-treated group (0.48-fold) than in the CBL0137-treated group (5.7-fold; P=0.0004) and in the gemcitabine-treated group (3.66-fold; P=0.0064). Comparison of median time to endpoint values for these groups gave the same result: there was no difference between the CBL0137 and gemcitabine groups, but combination of the two drugs led to an increase in median time to endpoint compared to either single drug treatment. Similarly, there was no difference in MST between the CBL0137 and gemcitabine monotherapy groups (40 and 48.5 days, respectively; P=0.2087), while there was a great difference between the gemcitabine monotherapy and CBL0137+gemcitabine combination groups (48.5 vs. 66 days; P<0.0001) and that between the CBL0137 monotherapy and CBL0137+gemcitabine combination groups was near-significant (40 vs. 66 days; P=0.0603). A single tumor-bearing mouse in the CBL0137 monotherapy group survived to the end of the study (Day 89). The tumor in this mouse (from the CBL0137-treated group) was, however, approaching the size endpoint when it was euthanized at the end of the study (1643 mm$^3$).

Overall, without wishing to be bound by theory, the FDA study results showed that with the exception of CBL0137 monotherapy, all drug treatments (monotherapies as well as double-drug combinations) were efficacious against patient-derived PDA#13756 tumor engrafts. The combination of gemcitabine+CBL0137 was found to be more efficacious than either drug alone. This treatment regimen led to complete tumor regression which was maintained for ~2 weeks after the end of the treatment period. In support of the PDA study results, without wishing to be bound by theory, the PDA results also showed that all drug treatments (monotherapies as well as double-drug combinations) were efficacious against patient-derived PDA tumor engrafts. The tested single-drug regimens (gemcitabine and CBL0137) were equally efficacious, and the CBL0137+gemcitabine double-drug regimen was more effective than the corresponding drugs administered as monotherapies.

Additionally, without wishing to be bound by theory, the H1975 NSCLC Study 1 analyses indicated that the combination of CBL0137+gemcitabine was more effective at suppressing H1975 tumor growth than either drug administered as a monotherapy. In support of these results, without wishing to be bound by theory, the H1975 NSCLC Study 2 data also indicated that combined treatment with CBL0137+gemcitabine produced greater efficacy than that of either single drug. The strength of the antitumor effect of the drug combination was illustrated by its ability to maintain suppression/regression of tumors well beyond the end the treatment phase of the study (mean tumor volume was ~1/2 of starting volume on Day 39 of the study).

Similar mouse studies as above were conducted in vitro to determine the possible mechanism of CBL0137+gemcitabine combination treatment on tumor suppression. FIG. 11 (Panels A-D) shows results from Western blots run from the PDA and H1975 NSCLC tumor-bearing mice treated with vehicle, 2 µM CBL0137, 2-25 µM gemcitabine, or CBL0137+gemcitabine treatment. Specifically, the Western blots monitored the effect of drug treatment on expression of markers of CBL0137 (SPT16 and SSRP1) and gemcitabine (ENT1, R1, and R2) activity in pancreatic (MiaPaca2 (FIG. 11, Panel A) and BxPC3 (FIG. 11, Panel B) and NSCLC (H1975 (FIG. 11, Panel C) and A549 (FIG. 11, Panel D) in vitro. Cells were treated for 2 h (SSRP1, SPT16) or 24 h (ENT1, R1, and R2). After the incubation, soluble protein lysates were prepared using 1×CCLR plus protease and phosphatase inhibitors. Specific protein bands were visualized by ECL. GAPDH was used as a loading control in the experiments. Without wishing to be bound by theory, ENT1 was not affected by CBL0137 or combination treatment, instead, CBL0137 blocked induction of R1 and R2 (ribonucleotide reductase subunits) when in combination. As monotherapy treatment, CBL0137 also appeared to cause a decrease in the R1 subunit, with effects being more prominent in PDA than NSCLC.

Additional in vitro studies were conducted in order to elucidate a possible mechanism of the CBL0137+gemcitabine combination treatment on tumor suppression. FIG. 12 (Panels A-F) shows the effect of CBL0137±gemcitabine treatment on the expression of CDA and dCK (two gemcitabine sensitivity related genes) in NSCLC and PDA cell lines following treatment with 2 µM CBL0137, 2-25 µM gemcitabine, or their combination. Expression was measured using real-time PCR with gene specific primers and probe. The latter was labeled with FAM. $B_2$-microglobulin was used as a control gene. Expression levels were determined by the ΔΔCt method. Error bars represent the standard error of the means. Without wishing to be bound by theory, CBL0137 abrogated CDA (cytidine deaminase) expression but not dCK (deoxycytidine kinase) in H1975 NSCLC and MiaPaca2 PDA cell lines. CBL0137 had no effect on CDA in A549. This cell line responded less to CBL0137 and was resistant to gemcitabine in one engraft experiment.

Taken together, without wishing to be bound by theory, the two in vitro experiments indicated that CBL0137 may enhance the antitumor activity of gemcitabine by downregulating genes/proteins involved in controlling gemcitabine sensitivity/resistance (e.g. cytadine deaminase and ribonucleotide reductase subunits).

Definitions

The following definitions are used in connection with the invention disclosed herein. Unless defined otherwise, at technical and scientific terms used herein have the same meaning as commonly understood to one of skit in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest, e.g. cancer.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. CBL0137 (and/or additional agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model, Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%, In some embodiments, the effect will result in a quantifiable change of about 10%, about 20%, about 30%, about 50%, about 70%, or even about 90% or more. Therapeutic benefit also includes halting or slowing the progression of the underlying disease or disorder or reduction in toxicity, regardless of whether improvement is realized.

In certain embodiments, a pharmacologically effective amount that will treat cancer will modulate the symptoms typically by at least about 10%, at least about 20%, at least about 30%, at least about 40%, or at least about 50%. In exemplary embodiments, such modulations will result in, for example, statistically significant and quantifiable changes in the numbers of cancerous cells or indicia of toxicity as described herein (e.g. number of certain cells in a blood test, number of liver enzymes in a blood test, etc.).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for treating hepatocellular carcinoma, comprising administering an effective amount of CBL0137 and a kinase inhibitor chemotherapeutic agent to a subject in need thereof, wherein the kinase inhibitor chemotherapeutic agent is sorafenib.

2. The method of claim 1, wherein the CBL0137 is administered after administration of sorafenib.

3. The method of claim 1, wherein the CBL0137 is co-administered with sorafenib.

4. The method of claim 1, wherein the CBL0137 and/or sorafenib is administered intravenously and/or orally.

5. The method of claim 1, wherein the CBL0137 and/or sorafenib is administered at a sub-therapeutic dose.

6. The method of claim 1, wherein the therapeutic window of CBL0137 and/or sorafenib is increased.

7. The method of claim 1, wherein the subject is undergoing treatment with sorafenib.

8. A method for treating pancreatic ductal adenocarcinoma or non-small cell lung cancer, comprising administering an effective amount of CBL0137 and a nucleoside analog chemotherapeutic agent to a subject in need thereof, wherein the nucleoside analog chemotherapeutic agent is gemcitabine.

9. The method of claim 8, wherein the CBL0137 is administered after administration of gemcitabine.

10. The method of claim 8, wherein the CBL0137 is co-administered with gemcitabine.

11. The method of claim 8, wherein the CBL0137 and/or gemcitabine is administered intravenously and/or orally.

12. The method of claim 8, wherein the CBL0137 and/or gemcitabine is administered at a sub-therapeutic dose.

13. The method of claim 8, wherein the therapeutic window of CBL0137 gemcitabine is increased.

14. The method of claim 8, wherein the subject is undergoing treatment with gemcitabine.

* * * * *